(12) United States Patent
Van Voris et al.

(10) Patent No.: US 6,319,511 B1
(45) Date of Patent: *Nov. 20, 2001

(54) TERMITE AND BORING INSECT BARRIER FOR THE PROTECTION OF WOODEN STRUCTURES

(75) Inventors: Peter Van Voris, Richland; Dominic A. Cataldo, Kennewick, both of WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/364,728

(22) Filed: Jul. 30, 1999

Related U.S. Application Data

(63) Continuation-in-part of application No. 08/482,300, filed on Jun. 7, 1995, now Pat. No. 6,060,076, which is a continuation-in-part of application No. 08/348,774, filed on Dec. 1, 1994, now abandoned, which is a continuation of application No. 08/117,877, filed on Sep. 7, 1993, now abandoned, which is a continuation of application No. 07/893,970, filed on Jun. 4, 1992, now abandoned, which is a continuation of application No. 07/401,955, filed on Sep. 1, 1989, now abandoned.

(51) Int. Cl.[7] ................ A01N 25/10; A01N 25/34; A01N 37/12; A01N 47/40
(52) U.S. Cl. ................ 424/411; 514/521; 514/531; 514/772.3; 514/953
(58) Field of Search ................ 424/411; 514/521; 514/531, 772.3, 953

(56) References Cited

U.S. PATENT DOCUMENTS

| Re. 32,356 | 2/1987 | Cardarelli | 428/78 |
|---|---|---|---|
| 1,999,458 | 4/1935 | Hollister | 47/1 |
| 2,269,626 | 1/1942 | Henry | 156/20 |
| 2,970,404 | 2/1961 | Beaufils et al. | 47/57.5 |
| 3,111,403 | 11/1963 | Soper | 71/2.3 |

(List continued on next page.)

FOREIGN PATENT DOCUMENTS

| 16980/83 | 7/1983 | (AU) . |
| 23427/84 | 8/1984 | (AU) . |
| 48655/90 | 8/1990 | (AU) . |
| 62329/90 | 3/1991 | (AU) . |
| 82443/91 | 2/1992 | (AU) . |

(List continued on next page.)

OTHER PUBLICATIONS

"Termfilm Termigranuls, The Anti Termite Solution", by Cecil Co., Oct. 18, 1996, 5 pages.

Termite Resistant Sheet for Moisture Permeable Building Material Obtained by Adding Anti–Termite Agent Into Laminated Sheet Obtained by Laminating Nonwoven Fabric or Woven Cloth onto Porous Polyolefin Sheet, 01058739/PN Mar. 6, 1989.

Database WPI Section CH Week 8547 Derwent Publications Lt. London GB Class A97 AN–85–293614.

Burton et al., "The Use of Controlled Release Herbicides in Waste Burial Sites", presented at the Eighth International Controlled Release Symposium, Fort Lauderdale, Florida, Jul. 26–29, 1981.

French Pat. 2,358,831. Chem. Abst. vol. 89, (1978), 158777f. Index Citation.

The Agrochemicals Handbook, 2$^{nd}$ Ed., D. Hartley, ed. The Royal. Society of Chemistry (1987). (39 selected pages).

(List continued on next page.)

*Primary Examiner*—S. Mark Clardy
(74) *Attorney, Agent, or Firm*—Jenkens & Gilchrist

(57) ABSTRACT

A method and device are disclosed which prevent the intrusion of insects into structures by using a controlled release device capable of releasing insecticide. In the disclosed method, the device maintains a minimal effective level of insecticide for a predetermined period of time.

57 Claims, 8 Drawing Sheets

U.S. PATENT DOCUMENTS

| | | | |
|---|---|---|---|
| 3,231,398 | 1/1966 | Pauli | 106/16 |
| 3,235,366 | 2/1966 | Seymour et al. | 71/2.6 |
| 3,257,190 | 6/1966 | Soper | 71/2.3 |
| 3,367,065 | 2/1968 | Cravens | 47/57.5 |
| 3,384,993 | 5/1968 | Kane | 71/64 |
| 3,502,458 | 3/1970 | Schenk | 71/64 |
| 3,551,192 | 12/1970 | Reinert | 117/138.8 |
| 3,592,792 | 7/1971 | Newland et al. | 260/41 |
| 3,608,062 | 9/1971 | Alfes et al. | 424/22 |
| 3,639,583 * | 2/1972 | Cardarelli et al. | 424/125 |
| 3,671,548 | 6/1972 | Itaya et al. | 549/79 |
| 3,691,683 | 9/1972 | Sterzik | 47/57.5 |
| 3,697,253 | 10/1972 | MacMurray | 71/97 |
| 3,705,938 | 12/1972 | Hyman et al. | 424/17 |
| 3,706,161 | 12/1972 | Jenson | 47/57.5 |
| 3,716,560 | 2/1973 | Taya et al. | 549/471 |
| 3,740,419 | 6/1973 | Campbell | 549/117 |
| 3,741,807 | 6/1973 | Horne | 134/24 |
| 3,759,941 | 9/1973 | Sampei et al. | 549/117 |
| 3,835,176 | 9/1974 | Matsuo et al. | 558/407 |
| 3,835,220 | 9/1974 | Matsui et al. | 424/40 |
| 3,846,500 | 11/1974 | Kitamura et al. | 568/660 |
| 3,851,053 | 11/1974 | Cardarelli | 424/78 |
| 3,857,934 | 12/1974 | Bernstein et al. | 424/30 |
| 3,864,114 | 2/1975 | Green | 71/3 |
| 3,864,388 | 2/1975 | Kitamura et al. | 560/60 |
| 3,867,542 | 2/1975 | Ueda et al. | 514/461 |
| 3,876,681 | 4/1975 | Okuno et al. | 560/124 |
| 3,880,643 | 4/1975 | Cooke et al. | 71/78 |
| 3,891,423 | 6/1975 | Stanley et al. | 71/86 |
| 3,899,586 | 8/1975 | Okuno et al. | 514/417 |
| 3,906,089 | 9/1975 | Okuno et al. | 424/45 |
| 3,939,606 | 2/1976 | Vandemark et al. | 47/9 |
| 3,954,814 | 5/1976 | Mizutani et al. | 549/449 |
| 3,966,963 | 6/1976 | Okuno et al. | 514/531 |
| 3,970,703 | 7/1976 | Kitamura et al. | 568/662 |
| 3,981,903 | 9/1976 | Hirano et al. | 560/124 |
| 3,998,868 | 12/1976 | Mizutani et al. | 560/124 |
| 4,003,945 | 1/1977 | Kitamura et al. | 560/124 |
| 4,007,258 | 2/1977 | Cohen et al. | 424/22 |
| 4,021,122 | 5/1977 | Krenmayr | 356/240 |
| 4,037,352 | 7/1977 | Hennart et al. | 43/129 |
| 4,063,919 | 12/1977 | Grano, Jr. | 71/11 |
| 4,065,555 | 12/1977 | Potter | 424/83 |
| 4,066,441 | 1/1978 | Lutz et al. | 71/121 |
| 4,077,795 | 3/1978 | Cooke et al. | 71/78 |
| 4,082,533 | 4/1978 | Wittenbrook et al. | 71/28 |
| 4,101,582 | 7/1978 | Lutz et al. | 260/574 |
| 4,102,991 | 7/1978 | Kydonieus | 424/27 |
| 4,104,374 | 8/1978 | Reuther et al. | 424/185 |
| 4,118,505 | 10/1978 | Kitamura et al. | 514/438 |
| 4,123,250 | 10/1978 | Kupelian | 71/78 |
| 4,160,335 | 7/1979 | Von Kohorn et al. | 43/131 |
| 4,172,904 | 10/1979 | Young et al. | 427/4 |
| 4,176,189 | 11/1979 | Itaya et al. | 514/389 |
| 4,190,680 | 2/1980 | Young et al. | 427/4 |
| 4,193,984 | 3/1980 | Kydonieus | 424/16 |
| 4,198,441 | 4/1980 | Young et al. | 427/2 |
| 4,198,782 | 4/1980 | Kydonieus et al. | 47/58 |
| 4,200,664 | 4/1980 | Young et al. | 427/4 |
| 4,205,096 | 5/1980 | Young et al. | 427/4 |
| 4,212,879 | 7/1980 | Ohsumi et al. | 514/427 |
| 4,212,897 | 7/1980 | Young et al. | 427/2 |
| 4,229,469 | 10/1980 | Mizutani et al. | 514/519 |
| 4,235,872 | 11/1980 | Tocker | 424/19 |
| 4,237,113 | 12/1980 | Cardarelli | 424/78 |
| 4,237,114 | 12/1980 | Cardarelli | 424/78 |
| 4,243,703 | 1/1981 | Palvarini et al. | 427/276 |
| 4,260,626 | 4/1981 | Carr et al. | 424/273 R |
| 4,263,463 | 4/1981 | Kitamura et al. | 568/873 |
| 4,269,626 | 5/1981 | Gorke et al. | 106/18.32 |
| 4,272,520 | 6/1981 | Kydonieus et al. | 424/84 |
| 4,279,924 | 7/1981 | Suzuki et al. | 514/521 |
| 4,282,207 | 8/1981 | Young et al. | 424/78 |
| 4,282,209 | 8/1981 | Tocker | 424/81 |
| 4,293,504 | 10/1981 | Suzuki et al. | 558/354 |
| 4,320,113 | 3/1982 | Kydonieus | 424/27 |
| 4,327,109 | 4/1982 | Mizutani et al. | 514/443 |
| 4,336,194 | 6/1982 | Ohsumi et al. | 548/562 |
| 4,344,250 | 8/1982 | Fahlstrom | 47/57.5 |
| 4,348,218 | 9/1982 | Bond, Jr. | 71/1 |
| 4,350,678 | 9/1982 | Palvarini et al. | 424/27 |
| 4,352,833 | 10/1982 | Young et al. | 427/4 |
| 4,360,376 | 11/1982 | Koestler | 71/121 |
| 4,374,126 | 2/1983 | Cardarelli et al. | 424/81 |
| 4,376,785 | 3/1983 | Matsuo et al. | 514/521 |
| 4,377,675 | 3/1983 | Daudt et al. | 528/25 |
| 4,400,374 | 8/1983 | Cardarelli | 424/78 |
| 4,405,360 | 9/1983 | Cardarelli | 71/117 |
| 4,435,383 | 3/1984 | Wysong | 424/78 |
| 4,457,929 | 7/1984 | Kamachi et al. | 424/246 |
| 4,496,586 | 1/1985 | Matsui et al. | 514/531 |
| 4,500,337 | 2/1985 | Young et al. | 71/67 |
| 4,500,338 | 2/1985 | Young et al. | 71/67 |
| 4,500,339 | 2/1985 | Young et al. | 71/67 |
| 4,503,071 | 3/1985 | Hirano et al. | 514/521 |
| 4,508,568 | 4/1985 | Fox | 106/2 |
| 4,576,801 | 3/1986 | Parry et al. | 427/288 |
| 4,579,085 * | 4/1986 | McGuire | 119/156 |
| 4,639,393 | 1/1987 | Von Kohorn et al. | 428/304.4 |
| 4,666,706 | 5/1987 | Farquharson et al. | 424/408 |
| 4,666,767 | 5/1987 | Von Kohorn et al. | 428/304.4 |
| 4,680,328 | 7/1987 | Dohrer et al. | 524/137 |
| 4,747,902 | 5/1988 | Saitoh | 156/244.11 |
| 4,767,812 | 8/1988 | Chapin et al. | 524/144 |
| 4,808,454 | 2/1989 | Saitoh | 428/40.6 |
| 4,818,525 | 4/1989 | Kamada et al. | 424/81 |
| 4,842,860 * | 6/1989 | Sugiura et al. | 424/403 |
| 4,886,656 | 12/1989 | Obayashi et al. | 514/144 |
| 4,921,703 | 5/1990 | Higuchi et al. | 424/419 |
| 4,929,497 | 5/1990 | Mitchell et al. | 428/265 |
| 4,971,796 | 11/1990 | Sjogren | 424/417 |
| 5,019,998 | 5/1991 | Cowen et al. | 364/496 |
| 5,083,408 | 1/1992 | Blom et al. | 52/57 |
| 5,104,659 | 4/1992 | Fishbein et al. | 424/411 |
| 5,116,414 | 5/1992 | Burton et al. | 71/121 |
| 5,135,744 * | 8/1992 | Alexander et al. | 424/78.17 |
| 5,139,566 | 8/1992 | Zimmerman | 71/121 |
| 5,181,952 | 1/1993 | Burton et al. | 504/347 |
| 5,201,925 | 4/1993 | Itzel et al. | 47/58 |
| 5,292,504 | 3/1994 | Cardin et al. | 514/65 |
| 5,296,227 | 3/1994 | Norval et al. | 424/411 |
| 5,317,834 | 6/1994 | Anderson | 47/48.5 |
| 5,439,924 | 8/1995 | Mills | 514/345 |
| 5,449,250 | 9/1995 | Burton et al. | 405/128 |
| 5,492,696 | 2/1996 | Price et al. | 424/417 |
| 5,525,147 | 6/1996 | Dunstan et al. | 106/18.3 |
| 5,801,194 | 9/1998 | Van Voris et al. | 514/531 |
| 5,856,271 | 1/1999 | Cataldo et al. | 504/360 |
| 5,860,266 | 1/1999 | Martinet et al. | 52/741.3 |
| 5,898,019 | 4/1999 | Van Voris et al. | 504/360 |
| 5,925,368 | 7/1999 | Van Voris et al. | 424/405 |
| 5,985,304 | 11/1999 | Van Voris et al. | 424/406 |
| 6,060,076 | 5/2000 | Van Voris et al. | 424/411 |
| 6,099,850 | 8/2000 | Van Voris et al. | 424/411 |

FOREIGN PATENT DOCUMENTS

| | | |
|---|---|---|
| 13886/95 | 8/1995 | (AU) . |
| 52454/96 | 12/1996 | (AU) . |
| 2 070 231 A1 | 12/1992 | (CA) . |
| 1 929 314 A | 6/1969 | (DE) . |

| | | |
|---|---|---|
| 0152976A | 8/1985 | (EP) . |
| 0 286 009 A2 | 10/1988 | (EP) . |
| 0 594 892 A1 | 5/1994 | (EP) . |
| 2 358 831 | 2/1978 | (FR) . |
| 2 018 593 A | 10/1979 | (GB) . |
| 2 098 541 A | 11/1982 | (GB) . |
| 52-72802 | 6/1977 | (JP) . |
| 58 39601 | 3/1983 | (JP) . |
| 5811 3102 | 7/1983 | (JP) . |
| 602 02801 A | 10/1985 | (JP) . |
| 64-58739A | 3/1989 | (JP) . |
| 6294165 A2 | 10/1994 | (JP) . |
| 8302080 A | 11/1996 | (JP) . |
| WO 84/02447 | 7/1984 | (WO) . |
| WO 90/14004 | 11/1990 | (WO) . |
| WO 92/03927 | 3/1992 | (WO) . |
| WO 95/18532 | 7/1995 | (WO) . |
| WO 97/47190 | 12/1997 | (WO) . |
| WO 98/21960 | 5/1998 | (WO) . |
| 86/1133 | 2/1986 | (ZA) . |

OTHER PUBLICATIONS

The Pesticide Manual., $8^{th}$ Ed., C. Worthington, Ed., British Crop Protection Council, 1987, pp. 7179–7180. (Table of Contents and 146 selected pages).

Kumar, et al., "The Effect . . . Treated Wood," J. Timber Dev. . . . India (1977), 23(3), pp. 9–13.

Offenlegunsschrift 1929314; Chem. Abstracts vol. 88 entry 75 506 V.

Morrell, J., Woodpole Conference Proceedings, 03/10–11/86. (Table of Contents and 101 selected pages).

PNL–3000–6/UC–70 Nuclear Waste Management Quarterly Progress Report, Apr. through Jun. 1980. Sep. 1980. Prepared for the U.S. Department of Energy under Contract DE–AC06–76RLO 1830, "Application of Long–term Chemical Biobarriers for Uranium Tailings". By J.F. Cline—Project Manager, pp. 22.1 and 22.2.

Zable, R. et al. The Fungal Associates, Detection, and Fumigant Control of Decay in Treated Southern Pine Poles, Final. Report EL–27GA for EPRI Research Project 47191, State University of New York, 1982. (Table of Contents and 95 selected pages).

Graham et al. "Controlling Biological Deterioration of Wood with Volatile Chemicals", EPRI Report EL–1480 (Oregon State University) 1980. (Table of Contents and 83 selected pages).

Dickinson, Morris and Calver, Boron as a Preservative Against Internal Decay, Distrib. Dev., Mar. 1989, v 89:1, pp. 9–14.

Zahora and Corden, Gelatin Encapsulation of Methylisothiocyanate for Control of Wood–Decay Fungi, Forest Products Journal, vol. 35 (7/8): pp. 64–69, 1985.

Groundline Repair for Wood Poles, EPRI Journal, vol. 11, No. 3, Apr./May 1986.

Burton, et al., "A Controlled–Release Herbicide Device for Multiple–Year Control of Roots at Waste Burial. Sites," Journal of Controlled Release (1986), pp. 47–54.

Chang, et al., "Control of Ant Damage to Polyethylene Tubes Used in Drip Irrigation Systems in Hawaiian Sugarcane Fields," International. Society of Sugar Cane Technologists (02/01–11/80), pp. 1686–1692.

Chen, et al., "Approaches to the Improvement of Biological Resistance of Wood through Controlled Release Technology," Proceedings of the 13th Int'l Symposium on Controlled Release of Bioactive Material.s (08/3–6/86), pp. 75–76.

Batelle Technology Transfer Bulletin, "Controlled–Release Chemicals for Inhibiting Plant Roots," 2 pp. (12/84).

Hughes, "Controlled Release Technology Inhibits Root Growth," Controlled Release Business and Technology, 1989, p. 15.

Jury et al., "Behaviour Assessment Model for Trace Organics in Soil: I. Model Description," J. Environ. Qual., vol. 12, No. 4, pp. 558–564, (1983).

Jury et al., "Behaviour Assessment Model for Trace Organics in Soil: III. Application of Screening Model," J. Environ. Qual., vol. 13, No. 4, pp. 573–579, (1984).

Jury et al., "Behaviour Assessment Model for Trace Organics in Soil: IV. Review of Experimental. Evidence," J. Environ. Qual., vol. 13, No. 4, pp. 580–586, (1984).

Roseman et al., "Chapter 18: The Use of Controlled Release Herbicides in Waste Burial Sites," Controlled Release Delivery Systems Marcel Dekker, NY, (1983).

"Soil Fumigants are Remarkably Effective in Stopping Decay of Wood," Chemical. Week, p. 39, (Sep. 25, 1974). *Abstract.

Solie et al., "Simulation of Triflural in Diffusion in the Soil," Transactions of the ASAE, pp. 1463–1467, (1984).

Steyaart, "Proceedings, Eighty–Second Annual Meeting of the American Wood–Preservers' Association: Address," Crossties, vol. 68, No. 3, pp. 45–46, Mar. 1987.

Streile, "The Effect of Temperature on Pesticide Phase Partitioning, Trasnport, and Volatilization from Soil," Abstract of the Dissertation, (1984), 37 pages.

Van Voris et al., "Long–Term Controlled Release of Herbicides: Root–Growth–Inhibiting Biobarrier Technology," pp. 1–19. No date.

Probst et al., "Fate of Trifluralin in Soils and Plants", J. Agric. Food Chem., vol. 15, No. 4, Jul.–Aug. 1967, pp. 592–599.

Delcourt et al., Chem. Abst., Cytologia, vol. 41, No. 1, Jan. 1976, pp. 75–84.

Lignowski et al., "Trifluralin and Root Growth", Chem. Abst., Plant and Cell Physiology, vol. 76 (1972), pp. 701–708.

Chemical Abstracts, 88, 1978: 154553(m), p. 1177.

Baker and Lonsdale, "Controlled Delivery—an emerging use for membranes", Chemtech, Nov. 1975, pp. 668–674.

Burton et al., "Application of Controlled Release Technology to Uranium Mill Tailings Stabilization", presented at American Nuclear Society Topical Meeting on Waste Management, Feb. 23–26, 1981, Tucson, Arizona, pp. 1009–1021.

Burton et al., "A Controlled–Release Herbicide Device For Multiple–Year Control of Roots at Waste Burial Sites", $10^{th}$ International Symposium on Controlled Release of Bioactive Materials, Jul. 24–27, 1983, San Francisco, California, pp. 305–308.

Burton et al., "The Use of Controlled Release Herbicides in Waste Burial Sites", presented at the Eighth International Controlled Release Symposium, Fort Lauderdale, Florida, Jul. 26–29, 1981, pp. 291–300.

Kumar, et al., "The effect . . . treated wood," J. Timber Dev. . . . India (1977), 23(3), pp. 9–13.

Offenlegunsschrift 1929314; Chem. Abstracts vol. 88 entry 75 506 V.

Hayes, W.C., Extending Woodpole Life: Solving a $5 Billion Dollar a Year Program, Electrical World, pp. 41–47, Feb. 1986.

Sheperd, M., Managing America's Wood Pole Inventory, EPRI Journal., Sep. 1987, vol. 12, No. 6.

Zahora et al., Gelatin Encapsulation of Methylisothiocyanate for Control of Wood–Decay Fungi, Forest Products Journal, vol. 35 (7/8): pp. 64–69, 1985.

Douglas, J., Groundline Repair for Wood Poles, EPRI Journal, Apr./May 1986, pp. 29–31.

Cline et al., "Biobarriers Used in Shallow Burial Ground Stabilization," *Nuclear Technology*, vol. 58, pp. 150–53 (1982).

A. Pajak et al., "Morphological and Cytological Effects Brought About By Trifluralin on Pea (Pisum Sativum L.)", *Biuletyn Warzywniczy*, pp. 451–62, 1979(abstract provided as first page).

Y. Eshel et al., "Effect of Dinitroanilines on Solanaceous Vegetables and Soil Fungi", *Weed Science*, pp. 243–46, vol. 20, Issue 3, May 1972.

\* cited by examiner

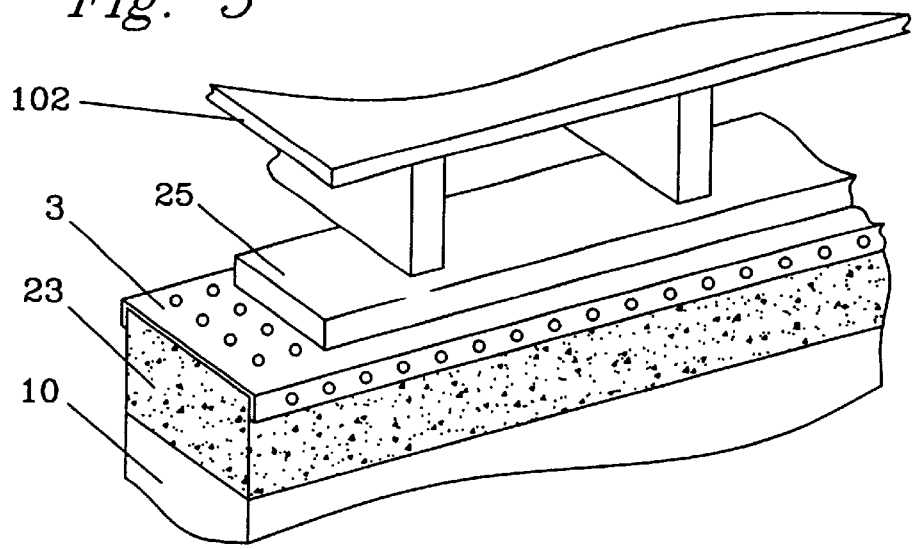
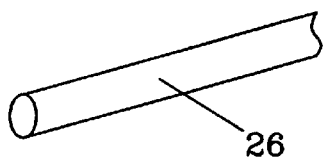
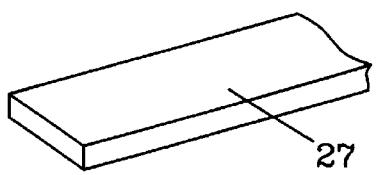
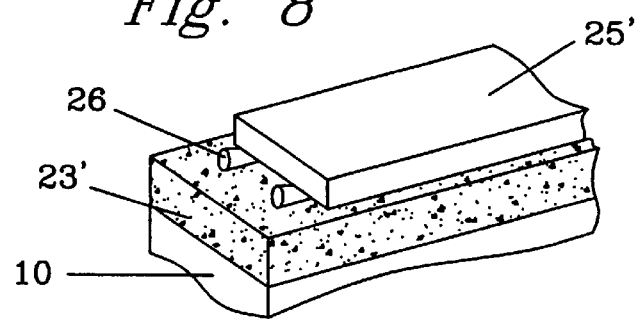
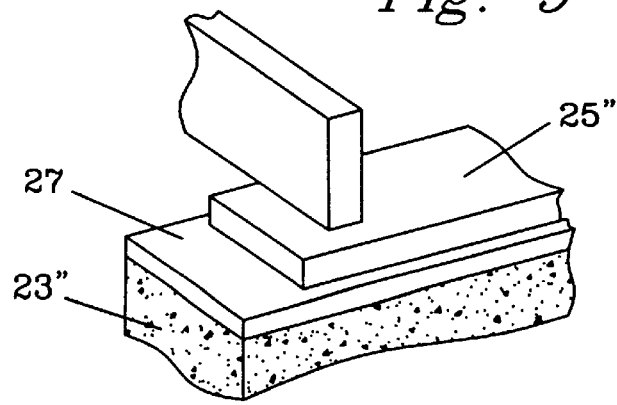

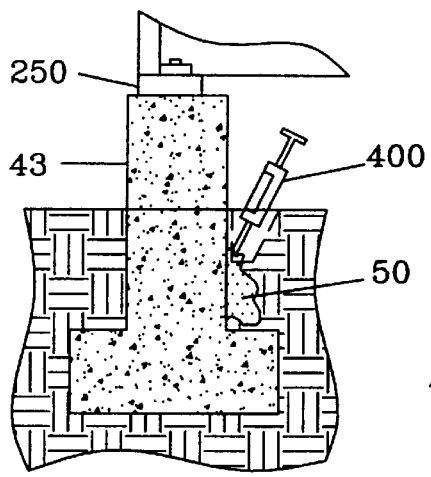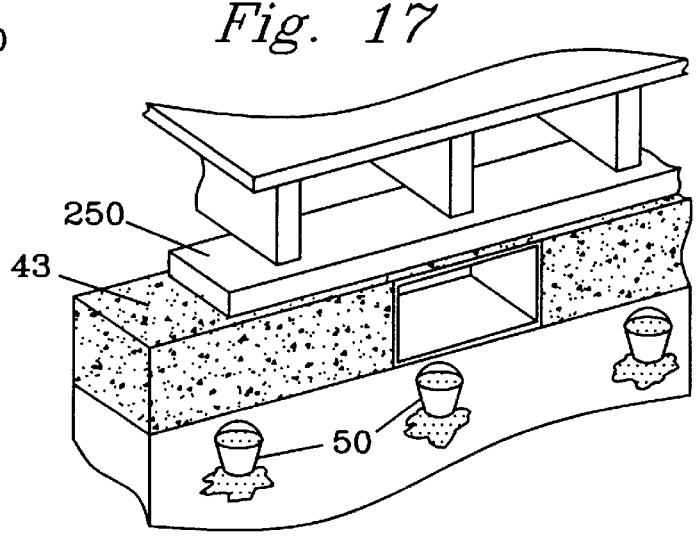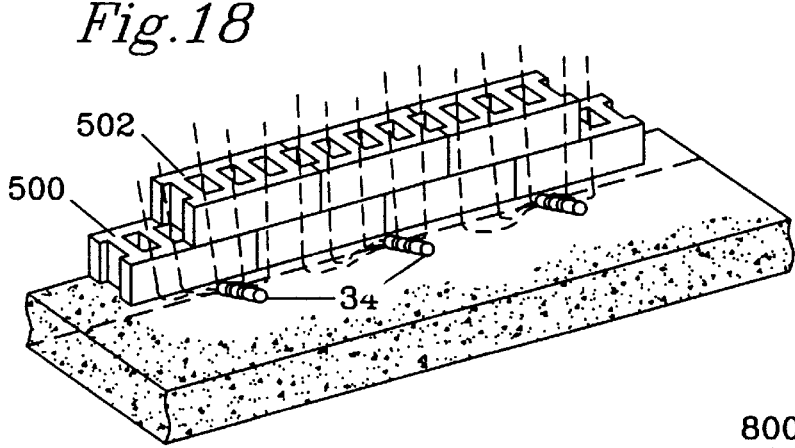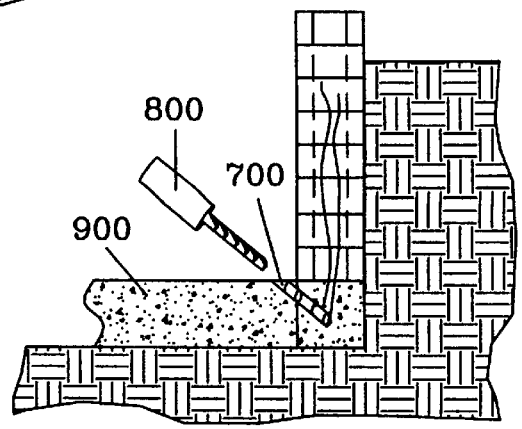

TERMITE AND BORING INSECT BARRIER FOR THE PROTECTION OF WOODEN STRUCTURES

CROSS REFERENCE TO RELATED APPLICATIONS

The present application is a continuation-in-part of U.S. patent application Ser. No. 08/482,300, filed on Jun. 7, 1995, which issued as U.S. Pat. No. 6,060,076, which is a Continuation-in-Part of U.S. patent application, Ser. No. 08/348,774 filed on Dec. 1, 1994, now abandoned which is a continuation of U.S. patent application, Ser. No. 08/117,877 filed on Sep. 7, 1993, now abandoned which is a continuation of U.S. patent application, Ser. No. 07/893,970 filed On Jun. 4, 1992, abandoned which is a continuation of U.S. patent application, Ser. No. 07/401,955 filed on Sep. 1, 1989 now abandoned.

FIELD OF THE INVENTION

The present invention relates to termite and boring insect barriers for the long-term protection of wooden structures. More particularly, it relates to a composition and method which creates and maintains an exclusion zone for insect pests such as termites, ants and other boring insects.

BACKGROUND OF THE INVENTION

Wood which is in contact with concrete, such as in wooden building construction and wood which is in contact with soil for example fence posts, utility poles, railroad cross-ties and wooden supports, can be structurally degraded by the action of termites, ants and other boring insects. Insecticides are available to protect wood from the action of such pests. Although insecticides are somewhat effective against the action of the boring insects, if insecticides are applied by themselves in sufficient quantity tD be effective over a period of time, they pose ecological concerns, human health, and may present unpleasant odors, soil leaching and volatility of the insecticide. Furthermore, even the greatest amounts of insecticides applied by themselves dissipate within a relatively short time and need to be reapplied.

A further disadvantage of conventional application methods is that the concentration of active ingredients resulting from a single application of insecticide starts out well above the minimum level necessary for effectiveness, but decreases rapidly and within a relatively short period of time drops below the minimal effective level necessary for a barrier.

To this end, a number of techniques for the controlled release of chemicals such as insecticides have become common in recent years. These methods employ polymer matrices and microcapsules to release insecticide.

Cardarelli U.S. Pat. No. 4,400,374 discloses the use of polymer matrices generally made of polyethylene, polypropylene, ethylene vinyl acetate, polyamide, polystyrene, polyvinyl acetate, or polyurethane to control the release of insecticides such as the insecticide commercially available under the tradename Dursban. The polymer matrices disclosed in U.S. Pat. No. 4,400,374, incorporate porosigen and a porosity reducing agent which upon contact with soil moisture or an aqueous environment dissolves the matrix.

Similarly, Cardarelli U.S. Pat. No. 4,405,360 relates to a polymer release matrix which can be composed of polyamide, polyurethane, polyethylene, polypropylene, polystyrenes and other polymers. The control release mechanism works in combination with a porosigen to release a herbicide in a moist environment.

In addition, Wysong U.S. Pat. No. 4,435,383 teaches the use of a controlled release mechanism for insecticides including carbamates, organothiophosphates, organophosphates, perchlorinated organics and synthetic pyrethroids. The release mechanism comprises a hydrophobic barrier monomer namely styrene and/or methyl styrene in combination with a monomer selected from one or more unsaturated mono- or di-carboxylic acids.

Another reference, Tocker U.S. Pat. No. 4,282,209 discusses a process for the preparation of insecticide-polymer particles. The insecticide, methomyl, is used to control insects which attack a tobacco, cotton or agricultural crops. Methomyl is dissolved with polymers such as polyamides, urethanes and epoxies to provide long-term residual insecticidal activity.

A second Tocker patent, U.S. Pat. No. 4,235,872, discloses the use of slow-release insecticide microcapsules having a core of methomyl surrounded by a cover of allaromatic, uncrosslinked polyurea. In the arrangement disclosed in this patent, methomyl is used to protect vegetables, field crops and fruit crops.

A sixth reference, Young et al. U.S. Pat. No. 4,198,441, discloses the use of insecticides such as Dursban in a controlled release matrix comprising an organopolysiloxane, a hydrolyzable silane and a hydrolyzable organic titanium.

Additionally, Young et al. U.S. Pat. No. 4,160,335 discloses a mode of dispersing insect control substances by applying stripes to sheets of cellophane. The insect control substance which can include Dursban is placed in a polymer as well.

Although the prior art does disclose the use of controlled release agents, none of the references teach the creation of a completely effective exclusion zone. It is desirable to create a zone so as to prevent any contact between the wood structure and insects capable of damaging such structures. An exclusion zone is necessary to protect wood structures for extended periods of time.

Therefore, in view of the above, it is an object of this invention to provide a zone of insecticide to protect wooden structures. Such zone consisting of a long term low volatility barrier and a high volatility short term barrier to protect adjacent soil.

It is a further object of this invention to maintain an exclusion zone for relatively great lengths of time or about 10 to 20 years.

SUMMARY OF THE INVENTION

The present invention provides a delivery system and method for the controlled release of insecticide which lasts for a predetermined period of time at a minimal effective level creating a zone in order to prevent an intrusion of insects such as termites, ants and other boring insects into wooden structures. The method utilizes a controlled release device which comprises a polymer selected from the group consisting of thermoplastic polymers, thermoset polymers, elastomeric polymers and copolymers thereof. By incorporating the insecticides into the polymers, the insecticides can be released at such a rate that they will continue to be effective as toxicants or repellents for insects capable of damaging wood structures for a prolonged period of time while at the same time maintaining sufficient concentrations to prevent insect penetration through the exclusion zone.

According to one aspect of this invention, there is provided a polymeric-carrier delivery system for the controlled release of insecticide comprising spun-bonded polymeric sheeting, and a bonded mixture of polymer and insecticide. The mixture of polymer and insecticide is next bonded to the polymeric sheeting. The sheeting with the bonded mixture of polymer and insecticide is then placed near a wooden structure to provide a means for a slow and relatively constant release of the volatile insecticide in order to create a barrier zone for insects in the soil around a wood structure. The polymers include thermoplastic polymers, thermoset polymers, elastomeric polymers as well as copolymers thereof and the insecticide comprises the family of insecticides known as pyrethrins.

According to another aspect of this invention, an exclusion zone is created by placing an extrusion near the wooden structure to be protected. The extrusion has a polymeric delivery system capable of controlled release of the insecticide. The carrier system maintains a steady and effective concentration of insecticide in the exclusion zone for great lengths of time.

According to another aspect of this invention, a pellet comprising a polymer and insecticide is provided to create and maintain an equilibrium concentration of insecticide for ants, termites and other wood boring insects in an exclusion zone for the wooden structure. The pellet is placed near a wooden structure to treat the soil in order to shield the wooden structure from termites, ants and other boring insects. The pellet can be placed near the structure by a variety of means. Additionally, the pellet can be embedded in a board or even included in a foam. In preferred embodiments the polymers include thermoplastic polymers, thermoset polymers, elastomeric polymers as well as copolymers thereof and the insecticide are pyrethrins.

According to another aspect of this invention, an exclusion zone is created by injecting a hot melt polymeric mixture. The controlled release device comprises one or more pyrethrins and the polymer is selected from the group consisting of thermoplastic polymer, elastomeric polymers and copolymers thereof.

According to further aspects of the invention, temperature driven controlled release devices are used to provide the exclusion zones.

According to another aspect of this invention, the controlled release device is used to fumigate structures.

The present invention, together with attendant objects and advantages, will be best understood with reference to the detailed description below read in conjunction with the accompanying drawing.

BRIEF DESCRIPTION OF THE DRAWINGS

FIG. 5 illustrates a third manner of using the embodiments of the invention shown in FIGS. 1 and 2 creating an exclusion zone.

FIG. 6 illustrates a third embodiment of the invention, in the form of a cylindrical extrusion.

FIG. 7 illustrates a fourth embodiment of the invention, in the form of a flat strip extrusion.

FIG. 8 illustrates a manner of creating an exclusion zone using the embodiment of the invention shown in FIG. 6.

FIG. 9 illustrates a manner of using the embodiment of the invention shown in FIG. 7 to create an exclusion zone.

FIG. 16 illustrates a hot-melt injection.

FIG. 17 illustrates the spacing of the hot-melt injunction.

FIG. 18 illustrates a plug fumigating cement blocks.

FIG. 19 illustrates a mode of applying plugs to fumigate cement blocks.

DETAILED DESCRIPTION

Figure 1:
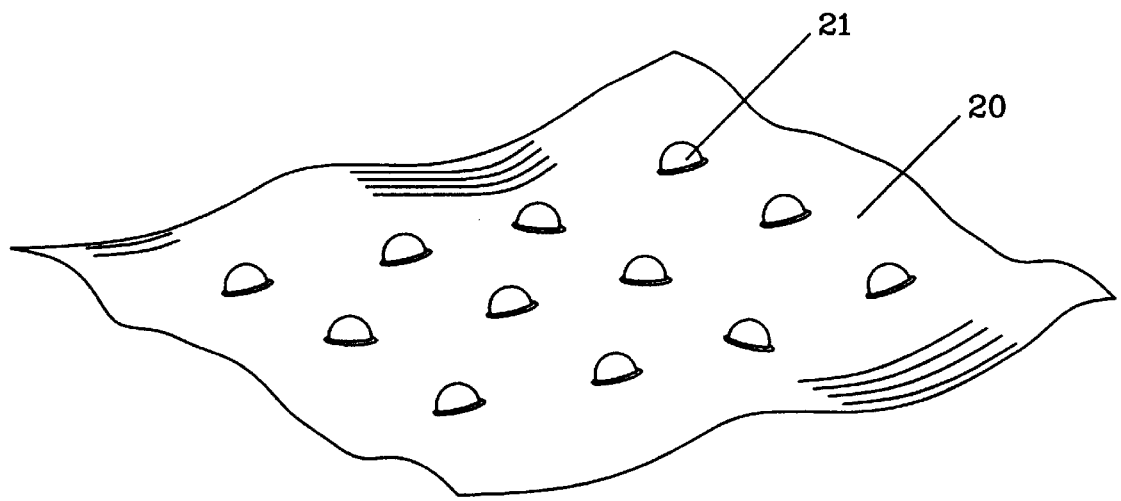
FIG. 1 illustrates a first embodiment of the invention, comprising spun-bonded polymeric sheeting, and a physical melt-bonded mixture of polymer and insecticide, wherein the mixture of polymer and insecticide is bonded in spots to the polymeric sheeting.

It has been found that there is a significant reduction of insects capable of damaging wood structures when an exclusion zone of insecticide is maintained for great lengths of time in the soil surrounding such structures. According to the present invention, the insecticide releases from a controlled release device comprising a polymer matrix system will last for at least 6 years.

A controlled release device refers to a substance that results in controlled and sustained release of an active chemical from its surface or to its surface. The device provides a method for controlled release of the chemical into the surrounding environment. The device releases insecticide at a high rate initially and a lower, steady rate thereafter. This release profile assures that the wooden object becomes protected in a relatively short period of time and that, subsequent to reaching the minimum effective level only the amount of insecticide necessary to replace the degraded insecticide is released. This release profile diminishes potential environmental and health problems of the treatment and reduces the cost of the treatment. A more detailed description of general principles of controlled release devices is given in U.S. patent application Ser. No. 06/555,113 filed Nov. 23, 1983 which is a continuation-in-part of Ser. Nos. 06/314,809 and 06/314,810 both filed on Oct. 26, 1981; Ser. No. 07/086,757, filed Aug. 18, 1987, Ser. No. 07/072,080, filed Jul. 10, 1987; and Ser. No. 07/091,918, filed Sep. 1, 1987, the contents of these applications being incorporated herein by reference. Methods for obtaining the release rates fire described in patent application Ser. No. 07/303,707, filed on Jan. 30, 1989.

The device provides a long-term solution by releasing the insecticide into the soil at a desired rate (10 $\mu g/cm^2$/day to 40 $\mu g/cm^2$/day) to create a zone (3–6 inches inclusive as measured from the device) having the Animal effective level of insecticide necessary (2 ppm for eastern subterranean termites, 4 ppm for formosan termites) to prevent insect intrusion. As used in this specification and the appended claims, the term Aminimal effective level is defined to mean the level of insecticide needed in the zone to prevent insects from approaching the zone, the specific level depends on the specific insect and the specific insecticide. Release rates from 0.4 $\mu g/cm^2$/day to 10 $\mu g/cm^2$/day may be used for smaller zone (less than 3 inches) or for different insect species deterred by lower (less than 2 ppm) soil concentration of insecticide.

The insecticides used in preferred embodiments should be U.S. Environmental Protection Agency approved insecticides to kill or repel termites, ants and other boring insects. The insecticide which is presently preferred for use in the present invention are pyrethrins, including tefluthrin, lambdacyhalothrin, cyfluthrin and deltamethrin. It will, however, be recognized by those skilled in the art that other effective insecticides such as isofenphos, fenvalerate, cypermethrin, permethrin and natural pyrethrin can also be used. These are available from a number of commercial sources such as Dow, Mobay, ICI, Velsicol and FMC respectively. A combination of insecticides, or one or more insecticides in combination with other active ingredients such as fungicides is also in accord with this invention.

A first embodiment of the invention, illustrated in FIG. 1, utilizes a polymeric-carrier delivery system for the controlled release of insecticide to generate an exclusion zone. The embodiment comprises spun-bonded polymeric sheeting 20, and a physical melt-bonded mixture of polymer and insecticide (shown as spots 21 in FIGS. 1 and 3–5). The spun-bonded polymeric sheeting 20 can be either a woven or non-woven textile or it can be a polymeric sheet. Such textiles can be obtained from a number of manufacturers such as Reemay, Exxon Fibers and Phillips Fibers. Preferably, the textile is woven or non-woven polypropylene.

The polymer in the melt-bonded mixture can comprise any number of thermoplastic polymers, thermoset polymers, elastomeric polymers or copolymers thereof. The selection of the polymers depends upon the desired release rate, the compatibility of the polymer with insecticide and upon environmental conditions. By way of example and not intending to limit the scope of this invention, the following polymers can be used: high density polyethylene, low density polyethylene, vinyl acetate, urethane, polyester, santoprene, silicone, or neoprene. However, the preferred polymers are high density and low density polyethylene. Although the above-mentioned insecticides can be used for best results, the insecticide should ideally comprise chlorpyrifos.

The mixture of polymer and insecticide may be placed on the spun-bonded polymeric sheeting in spots. These spots should be spaced so as to adequately maintain the amount of insecticide above the minimal effective level in an exclusion zone. The minimal effective level is the least amount of insecticide needed in a zone so as to prevent intrusion by insects. Spots 21 in FIGS. 1 and 3–5 are preferably about 0.5 to 1.5 centimeters in diameter, and about 0.5 to 1.5 centimeters in height. The size and shape of the spots will depend upon the user's preference and can be tailored to the job contemplated by the buyer. The spots 21 can be configured in rows with the spacing of the spots preferably being from about 1.5 to 4 centimeters from adjacent spots. It will be recognized by those skilled in the art that other configurations of spots can also be used depending on the particular application. The insecticide releasing polymeric sheet is placed near or around the wooden structure to create an exclusion zone by the controlled release of insecticide.

A second embodiment of the invention also utilizes a polymeric-carrier delivery system for the controlled release of insecticide comprising spun-bonded polymeric sheeting 20 and a physical melt-bonded mixture of polymer and insecticide. The polymeric sheeting 20 as in the first embodiment can be either woven or non-woven polypropylene upon which is bonded the physical melt-bonded mixture (shown as stripes 22 in FIG. 2). Similarly, the polymers and insecticide described above with respect to the first embodiment may also be used in the embodiment described in this section.

Figure 2:
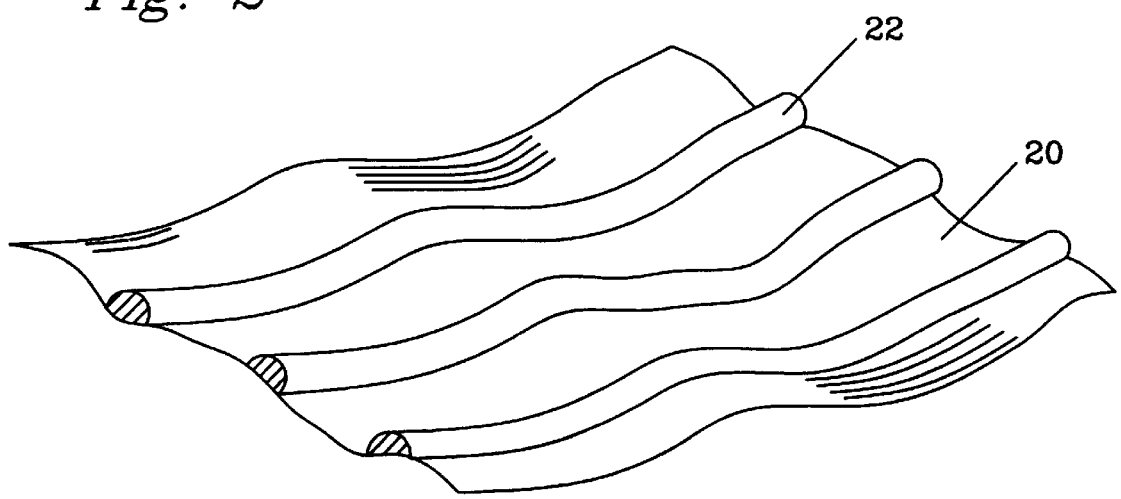
FIG. 2 illustrates a second embodiment of the invention, comprising spun-bonded polymeric sheeting, and a physical melt-bonded mixture of polymer and insecticide, wherein the mixture of polymer and insecticide is bonded in stripes to the polymeric sheeting.

The mixture of polymer and insecticide of the second embodiment may alternatively be placed on spun-bonded polymeric sheeting using extruder systems which provide stripes, e.g., as shown in FIG. 2. The stripes 22 can be about 1 centimeter in height, and about 5 to 15 centimeters apart. Optimally the stripes should be placed about 10 centimeters apart. It is desirable that the stripes should be configured in such an arrangement so as to permit a steady state concentration of insecticide in the exclusion zone after an initial burst of insecticide. After the stripes are applied to the polymeric sheet, the sheet is placed on or near the wooden structure to be protected from insects.

Filler and/or carriers may also be included in all of the embodiments of the invention. The inclusion of the filler and/or carrier permits greater amounts of insecticide to be loaded into the polymer while at the same time assisting in the control of the rate of release of the insecticide. The best results are observed by using carbon black as a filler and/or carrier, but clay or amorphous silica can also be used. Carbon black is preferred because it best serves to stabilize the polymer and increase the possible concentration of insecticide in the polymer while at the same time, permitting control of the polymer matrices' release rate.

If carbon black is utilized, the first step in producing the device is to melt the insecticide and mix it with the carbon black. The melted insecticide adheres to the extremely large surface area of the finely divided carbon black and the mixture is cooled for incorporation in the polymer. Polymers which may be used in a carbon black application are a polyethylene, polypropylene, copolymers or blends of polyethylene and polypropylene, polybutylene, epoxy polymers, polyamides, acrylate-styrene-acrylonitrile, aromatic or unsaturated polyesters, polyurethanes, silicones, or any other suitable polymers or copolymers thereof.

The carbon black-insecticide mixture in the first and second embodiments (or just insecticide, if carbon black is not used) is then mixed with the polymer, preferably polyurethane, in either the molten, powder or liquid stage. Next this mixture is bonded to the polymeric sheeting. In the first and second embodiments of the invention, the polymer and insecticide are melt-bonded to the polymeric sheeting.

Another mode of bonding the mixture of polymer and insecticide to the polymeric sheeting is by Athrough-injection molding, a technique which is known in the art. In Athrough-injection molding, molten material is injected from a heated nozzle through a porous web and into a mold. The molten material flows through the web under pressure and is solidified in the mold. While the molten material is being injected, the porous web allows air to escape, but it also retains the molten mass under pressure until it has cooled.

A different method of bonding the mixture of polymer and insecticide to the polymeric sheeting is by placing a melted mixture of polymer and insecticide on the spun-bonded polymeric sheeting. If the mixture is melted, it must be allowed to cool, cure and solidify. As used hereinafter, "a melted mixture of polymer and insecticide" is intended to indicate that the polymer is either melted or already in the liquid stage. The insecticide may also be melted or contained in a slurry solution, depending on its melting point. A "melted mixture of polymer and insecticide" can also contain carbon black or other additives which do not melt but flow with the melted polymer/insecticide mass.

The first and second embodiments of the invention should provide release rates sufficient to maintain an effective insecticide concentration in the exclusion zone to kill or repel insects but at sufficiently slow rates to maintain an effective concentration for an extended period of time. Overall, a preferred composition for the first and second embodiments of the invention comprises from about 70 to 95 parts by weight of carrier polymer, from about 0 to 15 parts by weight of carbon black, and from about 5 to 30 parts by weight of insecticide. The design considerations of the controlled release devices vary according to such factors as user preference and geographic conditions. The steady state release rate of the polymeric delivery system of these two embodiments after the initial burst of insecticide can be maintained for at least 6 years as a barrier to insects such as ants and termites. However, the equilibrium concentration of this embodiment can easily be adjusted to meet the specific needs of each user.

Optionally, the embodiments shown in FIGS. 1–5 may comprise an insecticide-impervious sheet (not shown) such as a metallized foil. The metallized foil or an extruded sheet of a polymer is laminated to one side of the spun-bonded polymeric sheeting in order to direct the flow of insecticide.

Figure 3:
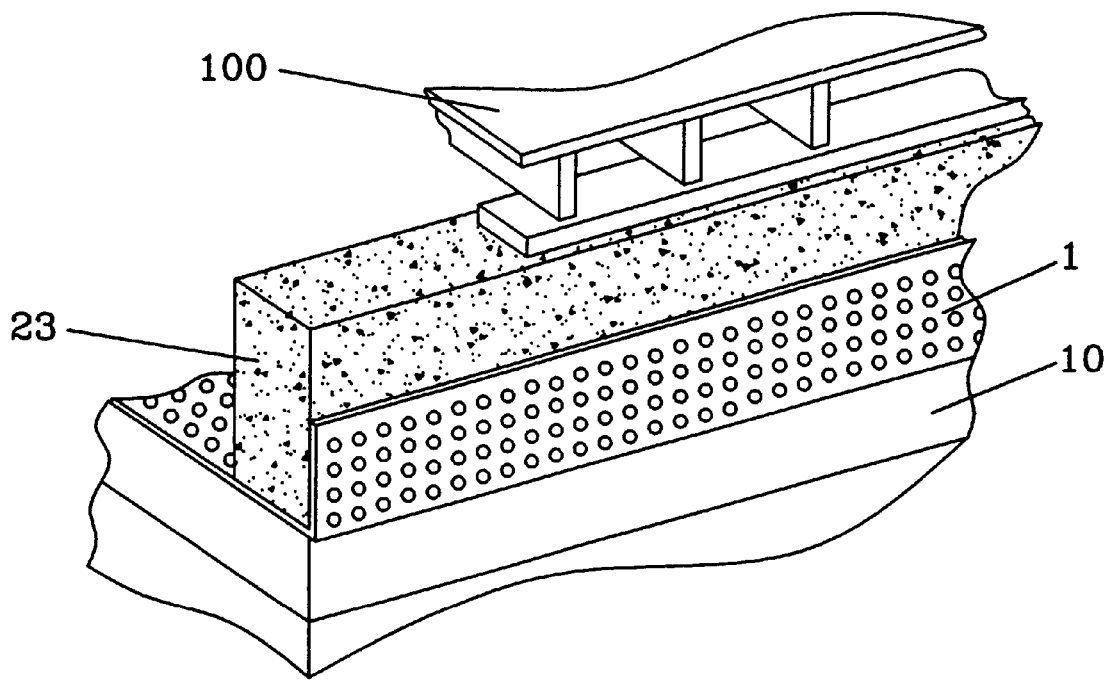
FIG. 3 illustrates a first manner of using the embodiments of the invention shown in FIGS. 1 and 2 and the exclusion zone created by the release of insecticide.
Figure 4:
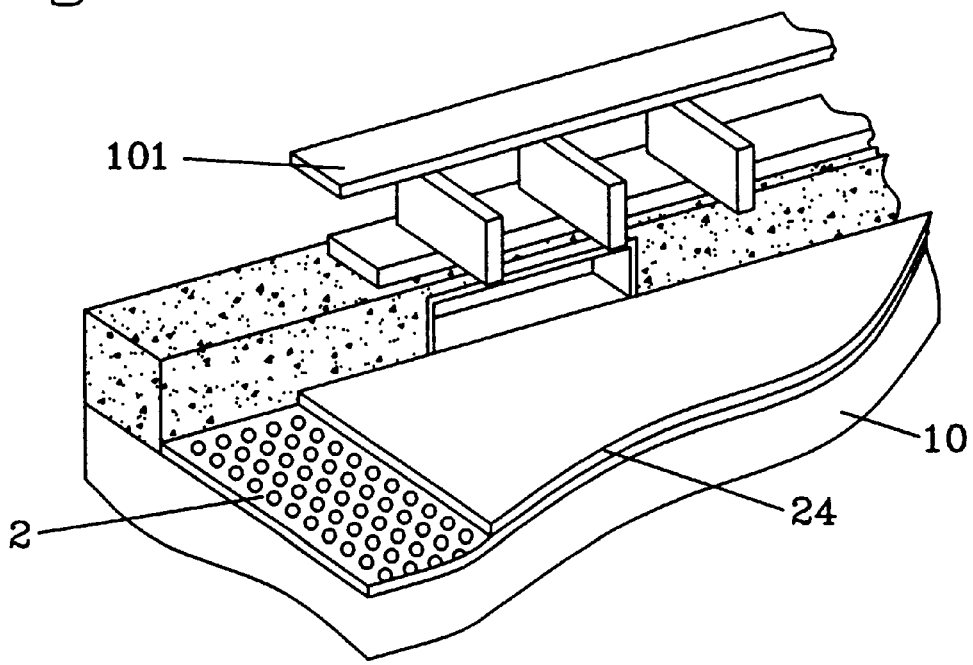
FIG. 4 illustrates a second manner of using the first and second embodiments of the invention to create an exclusion zone.

Once made, the polymeric-carrier delivery systems of the first and second embodiments are placed near the structure desired to be protected from insects. FIGS. 3–5 illustrate various applications of either the spotted or striped sheet embodiments of the invention. The FIG. 1 configuration is shown in FIGS. 3–5, but it is understood that the FIG. 2 configuration, or other configurations can work as well.

In FIG. 3, the polymeric-carrier delivery system 1 is placed under and alongside a concrete foundation 23 of a wooden structure 100 creating an exclusion zone 10 to protect the structure from termites, ants and other boring insects.

In FIG. 4, the polymeric-carrier delivery system 2 is placed under a structural member 24, such as a porch, patio, sidewalk, or under a basement foundation beside the wooden structure 101 to provide an exclusion zone 10.

In FIG. 5, the polymeric-carrier delivery system 3 is placed over and on the sides of the concrete foundation 23 of a wooden structure 102, but under the wooden portion 25 of the structure to create an exclusion zone.

Another embodiment of the invention is illustrated in FIGS. 6 and 7. This embodiment pertains to extrusions, such as extruded flexible cylinders 26 and extruded flexible flat strips 27 shown respectively in FIGS. 6 and 7. A wide variety of polymers which can be classified into four broad subgroups can be utilized. The groups include thermoplastic polymers, thermoset polymers, elastomeric polymers and copolymers of the three groups named above. By way of example, some polymers which can be used from the four groups are: high density polyethylene, low density polyethylene, EVA, vinyl acetate, urethane, polyester, santoprene, silicone, neoprene and polyisoprene. The preferred insecticide is chlorpyrifos although the insecticides described above can be used. Carbon black may also be added.

Cylinders preferably have a size ranging from about 5 to 15 millimeters in diameter, but most preferably about 10 millimeters in diameter for the optimal steady state delivery of insecticide into the exclusion zone. Flat strips should preferably have a thickness of from about 1 to 6 millimeters and a width of from about 5 to 15 millimeters. It, however, should be noted that both cylinders and flat strips can be designed to meet the varying conditions encountered by user.

Overall, in order to maintain an equilibrium concentration of insecticide in the exclusion zone for an extended period of time, the composition of this embodiment of the invention, should comprise from about 70 to about 95 parts by weight of polymer, from about 0 to about 30 parts weight of carbon black, and from about 5 to about 30 parts by weight of insecticide. The composition of the extrusion can, however, be tailored to the specific needs of the user. It is estimated that the exclusion zone can be maintained for at least 6 years for a cylinder and likewise for flat strips.

The extrusions can be positioned in a variety of positions to create exclusion zones. FIG. 8 illustrates a manner of using the extrusion shown in FIG. 6. One or more flexible cylinders 26 are placed between the concrete foundation 23' and the wooden portion 25' of the structure. The flexible cylinders 26 release insecticide at a controlled rate to create an exclusion zone. An advantage of this configuration is that flexible cylinders 26 can be placed under a structure that has already been built. Similarly, in a manner not shown, the flexible cylinders can be placed vertically into the ground as opposed lo horizontally. As will be recognized by those skilled in the art, the extrusions may have other suitable shapes and be placed in any suitable position depending upon the particular use contemplated.

FIG. 9 illustrates a manner of using the flexible flat strip extrusion shown in FIG. 7. One or more flexible flat strips 27 create an exclusion zone by being placed between or alongside the concrete foundation 23" and the wooden portion 25" of the structure. The flexible flat strips 27 can also be placed vertically alongside a wall in an embodiment not illustrated in the drawings. Again, any suitable placement of the flat strips is considered as being within the scope of the invention.

The controlled release of insecticide can also be conveniently achieved by using pellets as illustrated in the embodiments shown in FIGS. 10–13. The pellet 13 comprises polymer, insecticide and preferably also includes a filler. Various polymers can be used in this embodiment. They can comprise polymers of four subgroups consisting of thermoplastic polymers, thermoset polymers, elastomeric polymers and copolymers thereof. Polymer selection from these four subgroups depends upon design considerations with the preferable polymer being either high density polyethylene or low density polyethylene. In turn, the insecticide preferable comprises tefluthrin, but the following insecticides can also be used:

isofenphos, fenvalerate, cypermethrin, perrnethrin and other pyrethrins. For optimal results, a carrier such as carbon black, can also be incorporated into the mixture.

The pellet 31 releases insecticide at a controlled rate for an extended period of time in order to establish an exclusion zone. The composition for such a pellet needed for the maintenance of a zone in the soil is from about 70 to about 95 parts by weight of polymer, from about 0 to about 30 parts by weight of carbon black, and from about 5 to about 30 parts by weight of insecticide. Ultimately, the compositions of the pellet depend upon user preference.

The pellets can be any convenient size depending upon the intended use, such as 1 to 25 millimeters in diameter (or width and thickness, if rectangular) by 2 to 20 centimeters or more in length. Furthermore, in order to fit specific user needs, the dimension of the pellets and the concentrations of the insecticide can easily be adjusted. However, an exclusion zone can be maintained for at least 6 years.

Figure 10:
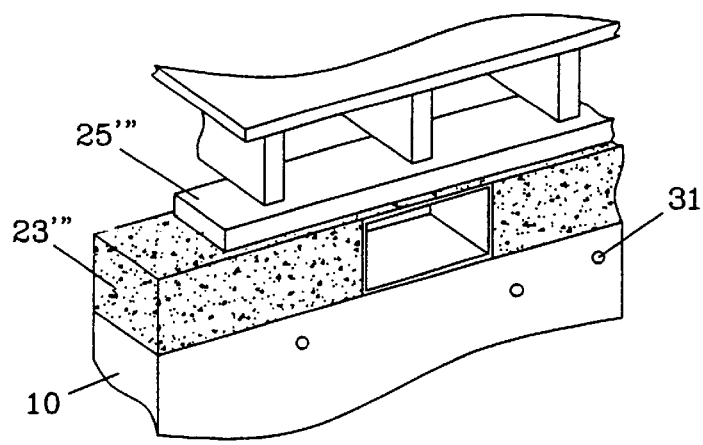
FIG. 10 illustrates another embodiment of the invention in the form of pellets wherein the pellets are being inserted into the ground near a wooden structure.
Figure 11:
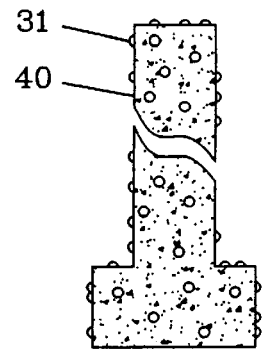
FIG. 11 illustrates a cross-sectional view of pellets placed on a surface.

Additionally, pellets 31 have the advantage that they can be conveniently placed most anywhere. The pellets of this embodiment of the invention are shown in FIG. 10. A pellet 31 is inserted near a wooden structure 25. The pellets as illustrated in FIG. 10 can be placed under a cement foundation 23''' or they can be placed directly under the wood structure (not illustrated) so as to permit the creation of a zone 10 surrounding the wooden structure 25''' to exclude insects capable of damaging such structures. FIG. 11 shows a cross-sectional view of pellets 31 inserted on a surface 40.

Figure 12:
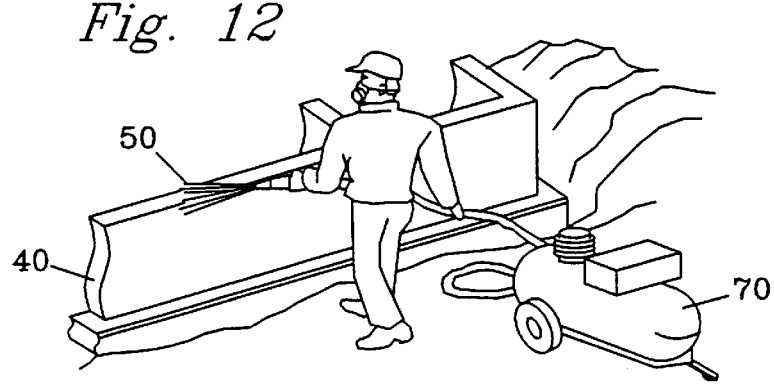
FIG. 12 illustrates the application of pellets to a concrete structure utilizing foam.
Figure 13:
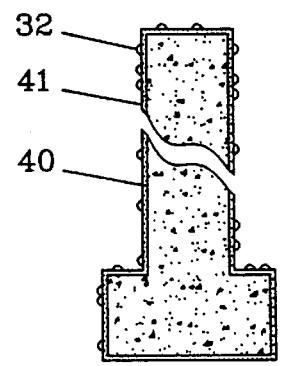
FIG. 13 illustrates a cross-sectional view of a concrete foundation after foam has been applied.
Figure 15:
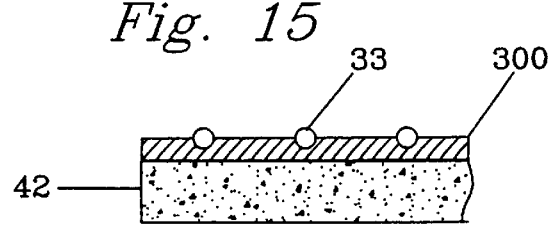
FIG. 15 illustrates a board containing pellets being applied to a concrete foundation.

Pellets are easily applied to a wide variety of uses. FIG. 12 illustrates pellets sprayed onto a concrete structure 41. FIG. 15 illustrates treating a surface by placing pellets 33 on preformed boards 300.

Pellets 32 are applied onto a surface 41 such as soil or concrete via a foam 50 as illustrated in FIG. 12. The pellets are first incorporated into a foam in a manner known in the art. The foam 50 containing the fine pellets is then sprayed as illustrated onto the surface 41 via a motorized sprayer 70 in FIG. 12 so as to provide a protective coating for the surface. The pellets then release the insecticide to create a protective barrier in the soil to protect the wood from harmful insects. For best results, the foam 50 is comprised of polyurethane. It is also possible to use silicone, polyester, or polyvinyl acetate. The pellets 32 can vary in size depending upon the foam thickness and the desired concentration of insecticide in the exclusion zone. The thickness of the foam to be applied to a surface can vary according to user's preference. The exclusion zone can be maintained for at least 6 years. In addition to being used as a carrier for insecticide, the foam also cures cement and acts as an insulator.

Figure 14:
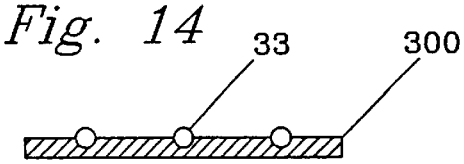
FIG. 14 illustrates pellets set on a board.

A preformed board with embedded pellets 33 can also be utilized as an embodiment of this invention as illustrated in FIG. 14. This board 300 can be made of any type of material which can suitably hold the pellets 33. Preferably, the board is comprised of styrofoam which is registered as a Dow trademark. The board can be applied in any variety of fashions and can also work as an insulating device. One manner of application is illustrated in FIG. 15, where the board 300 with pellets 33 is placed above a concrete surface 42. The embedded pellets are regularly spaced with the spacing being specified by the devised amount of insecticide.

In another embodiment as shown in FIGS. 16 and 17, the controlled release device comprising the polymer matrix and insecticide can be applied via a hot melt. This embodiment is designed to meet the needs of structures already in place. As stated above, the polymer matrix can comprise any of the four above-named polymer groups. Similarly, any of the above-named insecticides can be utilized. However, it is preferable to use high or low density polyethylene with either a pyrethrin. Although tailored to the user, the concentrations of the various substances in the hot-melt application should range from about 70 to about 95 for the polymer, from about 5 to about 30 for the insecticide and from about 0 to about 30 for filler/carrier for optimal results.

FIG. 16 shows hot melt 50 being injected by a syringe 400 into the ground near a concrete foundation 43. The concrete structure 43 supports a wooden structure 250. FIG. 17 shows the spacing between the hot melt 50 which has already been injected into the ground.

In another embodiment, FIGS. 18 and 19 illustrate the use of insecticide to fumigate a structure 500. By injecting or placing the controlled release device in or near a structure which can be fumigated, the insecticide release from the controlled release device can vaporize thereby fumigating the structure. FIG. 18 illustrates the use of plugs 34 to fumigate a structure 500 made of building blocks 502. Similarly, FIG. 19 illustrates a mode of applying the controlled release device by using a drill 800 to bore a hole 700 into a cement slab 900. Once inserted, the plug is able to fumigate the structure.

Currently Preferred Embodiment

The currently preferred product of employing the present invention comprises a polymer sheet, having thickness preferably in the range from about $\frac{1}{16}$ to $\frac{1}{8}$ inch and a low vapor pressure insecticide, preferably permethrin. The preferred polymers are polyurethane and polyethylene. Adjacent to and, preferably attached to the polymer sheet are additional controlled release devices. These devices are preferably in the form of elongated bars but can be in any suitable form, including pellets.

These additional devices preferably have a polymeric matrix made of EVA or, polyethylene and contain a higher vapor pressure pyrethrin such as tefluthrin. The sheet provides long term chemical contact protection. The additional devices associated with the sheet release the insecticide at a higher rate to provide a chemical barrier in the adjacent structure or soil.

This approach can also be used, for example, for sill plates. A controlled release strip of low vapor insecticide in a polymer matrix has associated therewith additional controlled release devices employing a higher vapor pressure insecticide. The strip acts as a contact protection against entry of insects and the additional controlled release devices release insecticides into concrete or wood to form a barrier in the concrete or wood to entry of insects.

The following examples are provided by way of explanation. As such, these examples are not viewed as limiting the scope of the invention as defined by the appended claims.

EXAMPLE 1

Experiments were conducted to determine the release rates of insecticides. The experimental approach involved an evaluation of polymer compatibility with chlorpyrifos. Furthermore, there was an analysis of release rates for the individual carrier delivery systems. Loading rates for the insecticide were held to either 5% to 10%, depending on polymer. Release rates were determined for all devices at 50° C.

Polymers evaluated included low melt polyethylene, polyurethane, two epoxies, silicone rubber, and a low melt polyethylene high in waxes to reduce thermal decomposition of the chlorpyrifos. Studies indicated that excessive thermal decomposition of the chlorpyrifos occurred at temperatures in excess of approximately 240° C.; thus, polymer selection was restricted to formulations not requiring excessive heat processing.

Table E1-1 1 provides a summary of the results from these studies. Overall, polymer compatibility with chlorpyrifos did not appear to present a problem with the loading rates employed. There was some loss of physical integrity of the polyurethane polymer employed, however, the other polymer systems exhibited no visible degradation at 50° EC. Release rates ranged from 10 $\mu g/cm^2/da$ for the silicone rubber, to 0.3 $\mu g/cm^2/da$ for Epoxy B.

TABLE E1-1

Polymer Formulations and Release Rates for Candidate Systems Employing Chlorpyrifos.

| Polymer Class | Chlorpyrifos Content (%) | Release Rate ($\mu g/cm^2/da$)[a] |
|---|---|---|
| Polyurethane | 5 | 2.1"1.4[b] |
| Epoxy A | 5 | <0.1 |
| Silicone | 5 | 10.3"3.5 |
| Urethane | 10 | 1.0"0.3 |
| Epoxy B | 10 | 0.3"0.1 |
| PE + Wax | 10 | 1.9"0.3 |

[a]Release rates performed at 50EC.
[b]Material exhibited excessive cracking at elevated temperature Using the data provided in Table E1-1, an estimated product longevity can be approximated. Assuming a device wt. of 0.5 g, with 10% load, then 50 mg of chlorpyrifos is available for release. Thus, for a polymer system having an area of 4 $cm^2$, and a release rate of 1 $\mu g/cm^2/da$, there is sufficient insecticide to last 30 years at elevated temperature. These rather simple calculations indicate that a variety of insecticidal products are possible.

EXAMPLE 2

Studies were also conducted with similar polymer systems as in Example E1-1 but with 80% pure pyrethrin. Release rates at 40° C. are provided in Table E2-1. The release rates were highest for urethane and silicone and lowest for the epoxies. Substantial variability in release rates were encountered and appropriate binders will need to be evaluated.

TABLE E2-1

Polymer Formulations and Release Rates for Candidate Systems Employing Pyrethrin I.

| Polymer Class | Pyrethrin I Content (%) | Release Rate ($\mu g/cm^2/da$)[a] |
|---|---|---|
| Epoxy A | 10 | 0.5"0.2 |
| Silicone | 10 | 21.2"5.4 |
| Urethane | 10 | 15.7"7.1 |
| Epoxy B | 10 | 0.2"0.1 |

[a]Release rates performed at 40° C.

From the data above, simple calculations can be performed to determine the possible life of the insecticide systems. As stated in Example E1-1, there are many variables which can alter the lifetime of an exclusion zone.

EXAMPLE 3

The following controlled release devices were made and tested to obtain their release rates. The devices were made as follows. All devices, except for those employing S-113 urethane, were injection molded into a thin sheet about ⅛ inch thick. The device employing S-113 urethane was cast, a method typically used for thermoset polymers. All thermoplastics were formulated using sufficient amount of carbon black to carry pesticides. All thermoplastic polymers were formulated with 10 percent pesticide, 3 or 7 percent carbon black to absorb liquid pesticide and 83 to 87 percent by weight of polymer. Specifically, devices made from thermoplastic polymers and deltamethrin and lambdacyhalothrin contained 3 percent of carbon black. The devices made from the remaining pesticides and thermoplastic polymers contained 7 percent of carbon black.

The devices made from S-113 urethane (a thermoset polymer) were made from a polymer mix containing 60% S-113, 40% castor oil and 5% of TIPA catalyst by weight. The polymer mix comprised 90% of the total weight of the device. The pesticide, deltamethrin, comprised the remaining 10% of the device. No carbon black was used in this device. The polymer/pesticide mixture was cast, using a spin caster into a ⅛ inch thick sheet and heated at about 60° C. for about 40 to 60 minutes to cure the cast sheet.

One inch squares were then cut from the thin sheets that were injection molded or cast and the squares were tested for release rates. The following release rates were obtained (Table E3-1):

TABLE E3-1

Release Rates

| Pesticide | Polymer | Release Rate ($\mu g/cm^2/day$) |
|---|---|---|
| Deltamethrin | S-113 urethane | 25.2 |
|  | Aromatic 80A | 16.8 |
|  | Pellethane 2102-80A | 8.8 |
|  | Pellethane 2102-55D | 8.0 |
|  | Alipmtic PS-49-100 | 7.2 |
| Cypermethrin | Polyurethane 3100 | 0.4 |
|  | Polyurethane 2200 | 0.7 |
|  | EVA 763 | 27.3 |
|  | Polyethylene MA7800 | 4.6 |
| Lambdacyhalothrin | Polyurethane 3100 | 0.4 |
|  | Polyurethane 2200 | 0.7 |
|  | EVA 763 | 20.6 |
|  | Polyethylene MA78000 | 4.6 |

TABLE E3-1-continued

Release Rates

| Pesticide | Polymer | Release Rate ($\mu$g/cm$^2$/day) |
| --- | --- | --- |
| Tefluthrin | Polyurethane 3100 | 6.4 |
| | Polyurethane 2200 | 25.0 |
| | EVA 763 | 40.4 |
| | Polyethylene MA78000 | 27.0 |
| Permethrin | Polyurethane 3100 | 1.4 |
| | Polyurethane 2200 | 1.3 |
| | EVA 763 | 28.5 |
| | Polyethylene MA78000 | 4.0 |

Further Preferred Embodiments

According to another aspect of the present invention, a method of making a controlled release device having a polymer, a carrier, and an active chemical, has the steps of:
(a) insuring that the active chemical is blendable with the carrier;
(b) removing moisture from the carrier;
(c) blending the active chemical with the dried carrier into a bound friable mixture;
(d) adding the bound friable mixture into an amount of a polymer preform and forming a formable mixture;
(e) forming the formable mixture into the controlled release device.

It is critical to the present invention that little or no polymer preform be present upon initial blending of the active chemical with the dried carrier to avoid development of flaws during forming.

The carrier is preferably a carbon product, for example activated carbon, carbon black, graphite or combinations thereof. Alternatively, the carrier may be an alumina, silicon-alumina, apatite or combination thereof. Apatite (calcium phosphate) is preferred for use with active chemicals which have lower absorption into other carriers, for example carbon black.

The polymer preform may be a polymer powder or a pre-polymer. The polymer preform may be any polymer, including but not limited to polyester, polypropylene, polyethylene, aromatic (e.g. styrene copolymer), specifically Kraton (a styrene block copolymer), polyurethane (e.g. Pellethane, Aromatic 80A, Aliphatic PS-49), aliphatic, polyolefins (e.g. polyisoprene, polybutadiene), a thermoset including but not limited to casting urethanes (e.g. solithane), polyolefins, epoxies, and combinations thereof, for example carboxylated latex with epoxy resin (Shell Hycar).

In a preferred method, the step of aciding involves
(i) dispersing the bound friable mixture into an amount of the polymer powder wherein the amount of the polymer powder is greater than the amount of bound friable mixture by weight thereby making a premixture; and
(ii) mixing the premixture with an additional amount of the polymer powder, wherein the additional amount is greater than the amount of the premixture by weight thereby making the formable mixture.
Alternatively, the step of adding may involve
(i) selecting an amine curable pre-polymer;
(ii) heating and mixing the pre-polymer with the active chemical and the bound friable mixture making a first solution;
(iii) heating and mixing a trialkanolamine with a soft segment cross-linker making a second solution; and
(iv) pouring the second solution together with the first solution into a combined solution and continuing heating while mixing said combined solution into a castable mixture. In this alternative embodiment, the forming step is by casting.

A controlled release device made in accordance with this first aspect of the present invention is estimated to have an active life from 2 months to over 60 years. Shorter life products (2 months to 2 years) are typically made from amine curable pre-polymer, whereas longer life products (2 years to over 60 years) are generally made from a thermoplastic, preferably with a carrier.

The active chemical is any chemical that is desired to be slowly released from the polymer, including but not limited to pesticides, perfumes, pheromones, air fresheners, drugs, and combinations thereof.

Certain active chemicals, for example trifluralin, are solid at room temperature and others (e.g. tefluthrin, perniethrin) are extremely viscous like grease or molasses. Active chemicals in a solid or highly viscous state are not blendable with a carrier. Accordingly, the active chemicals must be treated in a manner to bring their viscosity to a level that is blendable with the carrier. A preferred method is heating to decrease the viscosity of the active chemical. Heating is preferably from about 5° C. to about 10° C. above the melting point of the active chemical. Alternatively, the active chemical may be mixed with a solvent or mechanically sheared to reduce its viscosity. Other active chemicals (e.g. Endothall) are blendable with the carrier without treatment to reduce their viscosity. Thus, insuring that the active chemical is blendable with the carrier is defined as simply checking the viscosity of the active chemical and only treating to reduce viscosity for blendability with the carrier if necessary. Table 1 identifies several active chemicals and the temperature for heating to bring them to a blendable viscosity.

TABLE 1

Active Chemical Blendable Viscosity

| Active Chemical | Temperature (EC) | Viscosity |
| --- | --- | --- |
| Permethrin | 42 | Flowable |
| Cyfluthrin | 65 | Flowable |
| Lambdacyhalthrin | 55 | Flowable |
| Tefluthrin | 51 | Flowable |
| Resmethrin | 55 | Flowable |
| Deltamethrin | 120 | Flowable |
| Trifluralin | 58 | Flowable |

The presence of water may lead to flaws in the form of bubbles or voids in thermoset or thermoplastic materials when they are formed. Additionally, moisture on the carrier can inhibit absorption of the active chemical. Accordingly, the carrier is dried to remove any moisture. Drying may be by heating or by exposure to a desiccant.

The active chemical and carrier are blended in sufficient amounts to produce a bound friable mixture. The bound friable mixture is characterized by small granules of carrier powder particles adhering to active chemical similar to concrete or mortar with insufficient water. The ratio by weight of active chemical and carrier to achieve a bound friable mixture will vary depending upon the active chemical and the carrier. Table 2a provides examples of approximate amounts of particular active chemicals and carriers that have been found to provide a bound friable mixture. When high release rates are needed early in product life, a weight ratio of active chemical to carbon black of about 0.5 is used.

For moderate levels of early release and longer longevity a weight ratio of about 2 is used. For longer longevities and slow release of a large reserve of active chemical a ratio of about 4 is used.

TABLE 2a

Bound Friable Mixtures

| Active Chemical (AC) | Carrier (C) | AC/C Wt Ratio |
| --- | --- | --- |
| Tefluthrin | Carbon Black[a] | 0.5–4.0 |
| Lambdacyhalthrin | Carbon Black | 0.5–3.0 |
| Permethrin | Carbon Black | 0.5–3.0 |
| Deltamethrin | Carbon Black | 0.5–4.0 |

[a]Carbon Black is Vulcan XC-72

Table 2b provides examples of the ratios by weight of active chemical to polymer absorbable within the polymer with and without a carrier. Comparing columns 3 and 4 of Table 2b, shows that addition of a carrier greatly enhances the amount of active chemical in the controlled release product.

TABLE 2b

Weight Ratio of Active Chemical to Polymer With and Without Carbon Black (CB)

| Active Chemical (AC) | Polymer (P) | AC/P Wt Ratio | AC/P Ratio (5 wt % CB) |
| --- | --- | --- | --- |
| Permethrin | LDPE 763[a] | 1.8 | 2.3 |
| Permethrin | Urethane 2200[b] | 0.5 | 0.8 |
| Tefluthrin | LDPE 763 | 1.7 | 2.2 |
| Tefluthrin | Urethane 2200 | 0.3 | 0.6 |

[a]LDPE 763 is a low density polyethylene, specifically Microthene 763-00
[b]Urethane 2200 is BF Goodrich Polyurethane 2200 Type 58134NAT 025D The bound friable mixture is mixed with an amount of dispersable polymer powder making a premixture to achieve about 10 wt % active chemical in the final controlled release product. It is preferred that the dispersable polymer powder be a thermoplastic. The amount of dispersable polymer powder is greater than the amount of the bound friable mixture by weight. Preferred weight ratios of dispersable polymer to bound friable mixture range from about 10 to about 200. The purpose of the premixture is to develop a homogeneous dispersion of bound friable mixture in polymer powder. Although a homogeneous dispersion may be achieved with higher ratios of dispersable polymer powder to bound friable mixture, more mixing time is required, and it is more difficult to avoid lumps.

Upon obtaining a premixture that is substantially homogeneous, additional mixable polymer powder is added to make a formable mixture. The mixable polymer powder may be the same as or different from the dispersable polymer powder. The mixable polymer powder may be of the same or different particle size or of the same or different chemical composition or any combination thereof. It is preferred that the mixable polymer powder be a thermoplastic.

The formable mixture may be formed by any plastic forming process, for example extrusion. It has been found that extrusion of the formable mixture of the present invention results in flaw free controlled release devices. Moreover, the controlled release devices made according t) the present invention have a more predictable life. This is because absence of flaws in the form of voids or bubbles reduces the opportunity for the active chemical to freely travel through flaws thereby increasing the life of the controlled release product.

EXAMPLE 4

Several formulations of active chemical, carrier and polymer were made according to the present invention (See Tables E4-1 and E4-2) to determine release rate of active chemical and biological efficacy.

Release rates reported in Tables E4-1–E4-4 were measured after cleaning product surfaces to remove any active material that may have been on the product surfaces after product forming. The carrier used was carbon black, specifically Vulcan XC-72.

Some of the entries in the Tables E4-1–E4-4 have two values for release rate. The first is the "brand new" release rate and the second is the release rate after the controlled release product had been in the field for from 4–6 months. Several of the formulations from Tables E4-1–E4-4 were used for efficacy tests, specifically toxicity studies.

TABLE E4-1

Formulation and Release Rate

| Active Chemical | Carrier (Carbon Black) | Polymer | Release Rate ug/cm$^2$/d |
| --- | --- | --- | --- |
| Diazinon | | | |
| 10 wt % | 10 wt % | HDPE[a] | 11.7 |
| 10 wt % | 10 wt % | LDPE | 17.6 |
| Chlorpyrifos | | | |
| 10 wt % | 10 wt % | HDPE | 28.1 |
| 10 wt % | 10 wt % | LDPE | 45.3 |
| 6 wt % | 0.5 wt % | Polyester | 1.86 |
| 6 wt % | 0.5 wt % | Polypropylene | 25.6 |

[a]HDPE is a high density polyethylene, specifically Polyethylene MA778000

TABLE E4-2

Formulation and Release Rate

| Active Chemical | Carrier (CB) Polymer | Release Rate |
| --- | --- | --- |
| Cyfluthrin | | |
| 10 wt % | 10 wt % HDPE | 1.2 |
| 20 wt % | 10 wt % HDPE | 1.6 |
| 20 wt % | 10 wt % LDPE 763 | 5.8 |
| 10 wt % | 5 wt % LDPE 763 | 12 |
| 10 wt % | 10 wt % LDPE 763 | 27.4 |
| 3 wt % | 0.5 wt % Hytrel[a] | 2.6 |
| 3 wt % | 0.5 wt % Polypropylene | 6.1 |
| Resmethrin | | |
| 10 wt % | 10 wt % LDPE 763 | 0.39 |
| 10 wt % | 10 wt % Hytrel | 1.2 |
| 10 wt % | 10 wt % Urethane 2200 | 0.44 |
| 10 wt % | 10 wt % LDPE 763 | 0.39 |
| Permethrin | | |
| 10 wt % | 10 wt % LDPE 763 | 12 |
| 10 wt % | 10 wt % Hytrel | 4.4 |
| 10 wt % | 10 wt % Urethane 2200 | 1.6 |
| 10 wt % | 5 wt % HDPE | 2.2–1.5 |
| 20 wt % | 10 wt % LDPE 763 | 37 |
| 5 wt % | 2.5 wt % Urethane 2200 | 1.9 |
| 10 wt % | 5 wt % LDPE 763 | 3.9 |
| 10 wt % | 10 wt % LDPE 763 | 8.9 |
| 10 wt % | 5 wt % LDPE 763 | 3.9 |

[a]Hytrel is a polyester

TABLE E4-3

Formulation and Release Rate

| Active Chemical | Carrier (Carbon Black) | Polymer | Release Rate ug/cm²/d |
|---|---|---|---|
| Tefluthrin | | | |
| 2 wt % | 1 wt % | HDPE | 0.52 |
| 5 wt % | 0 wt % | HDPE | 1.6 |
| 5 wt % | 2.5 wt % | HDPE | 5.3–2.1 |
| 5 wt % | 5 wt % | HDPE | 1.1 |
| 5 wt % | 10 wt % | HDPE | 0.56 |
| 5 wt % | 20 wt % | HDPE | 2.3 |
| 10 wt % | 0 wt % | HDPE | 1.9 |
| 10 wt % | 5 wt % | HDPE | 5.3–4.4 |
| 10 wt % | 10 wt % | HDPE | 1.4 |
| 10 wt % | 20 wt % | HDPE | 1.2 |
| 10 wt % | 40 wt % | HDPE | 5.5 |
| 10 wt % | 5 wt % | LDPE 763 | 6.9–5.0 |
| 5 wt % | 2.5 wt % | LDPE 763 | 7.0–4.2 |
| 20 wt % | 10 wt % | Urethane 2200 | 18 |
| 5 wt % | 2.5 wt % | Polypropylene | 6.0 |
| 10 wt % | 5 wt % | Polypropylene | 6.9 |

TABLE E4-4

Formulation and Release Rate

| Active Chemical | Carrier (Carbon Black) | Polymer | Release Rate ug/cm²/d |
|---|---|---|---|
| Lamdacyhalthrin | | | |
| 2 wt % | 1 wt % | HDPE | 0.8 |
| 5 wt % | 0 wt % | HDPE | 1.3 |
| 5 wt % | 2.5 wt % | HDPE | 2.0–1.0 |
| 5 wt % | 5 wt % | HDPE | 1.0 |
| 5 wt % | 10 wt % | HDPE | 0.8 |
| 5 wt % | 20 wt % | HDPE | 1.1 |
| 10 wt % | 0 wt % | HDPE | 1.4 |
| 10 wt % | 5 wt % | HDPE | 2.8–1.2 |
| 10 wt % | 10 wt % | HDPE | 1.5 |
| 10 wt % | 20 wt % | HDPE | 2.4 |
| 10 wt % | 40 wt % | HDPE | 2.3 |
| 1 wt % | 0.5 wt % | LDPE 763 | RR < 0.1 |
| 5 wt % | 2.5 wt % | LDPE 763 | 2.9–1.1 |
| 10 wt % | 5 wt % | LDPE 763 | 8.3–8.8 |
| 20 wt % | 10 wt % | LDPE 763 | 12 |
| 1 wt % | 0.5 wt % | Polyurethane | RR < 0.1 |
| 5 wt % | 2.5 wt % | Polyurethane | 4.4 |
| 10 wt % | 5 wt % | Polyurethane | 7.3 |
| 1 wt % | 0.5 wt % | Polyureth/LDPE | 2.6 |
| 5 wt % | 2.5 wt % | Polyureth/LDPE | 5.5 |
| 10 wt % | 5 wt % | Polyureth/LDPE | 8.3 |

Fire Ants

Pot liners were made for testing against fire ants. The pot liners contained either chlorpyrifos or cyfluthrin with 0.5 wt % carbon black in either polyester or polypropylene. Pot liners lacking both chlorpyrifos and cyfluthrin were used as controls. Pot liners were supplied to the USDA Imported Fire Ant Station in Gulfport Miss. in 1992. Pot liners were placed into standard 1 gallon containers with untreated soil media and placed outdoors to age under simulated nursery conditions. Aged pots were then placed within fire ant population areas and monitored monthly for occupation and avoidance behavior. Initially, there was no fire ant occupation of the pots containing chlorpyrifos or cyfluthrin. Occupation occurred in the untreated pots. After 9 months, the pots having 3 wt % active chemical remained unoccupied whereas the other treated pots were occupied. After 16 months, the 3 wt % active pots were still unoccupied. During part of the study, desiccation was used to force the fire ants to choose between the pots and the desiccated soil. Fire ants initially entered treated pots, then left and died external to the pots, or they moved as far as possible from the pots and died.

Flies

Contact strips for controlling flies were made with resmethrin and permethrin of 10 wt %, carbon black of 10 wt % and using thermoplastic polyurethane 2200 (Polyu2200), Hytrel thermoplastic polyester polymers (Microthene 763). The average dead fly-count was 7.3 flies per window per week before and after use of the treated strips. The strips were placed in a window and observed for two weeks. The results are shown in TABLE E4-5.

TABLE E4-5

Dead Fly Count

| Active Chemical | Polymer | Fly Count Flies/window/week |
|---|---|---|
| Resmethrin | Microthene 763 | 18.5 |
| Resmethrin | Hytrel | 23 |
| Permethrin | Urethane 2200 | 30 |
| Permethrin | Microthene 763 | 48 |

Release rates for resmethrin ranged from 0.4–1.2 ug/cm²/day whereas release rates for permethrin ranged from 1.6–12.0 ug/cm²/day which was more effective.

Termites

Figure 20A:
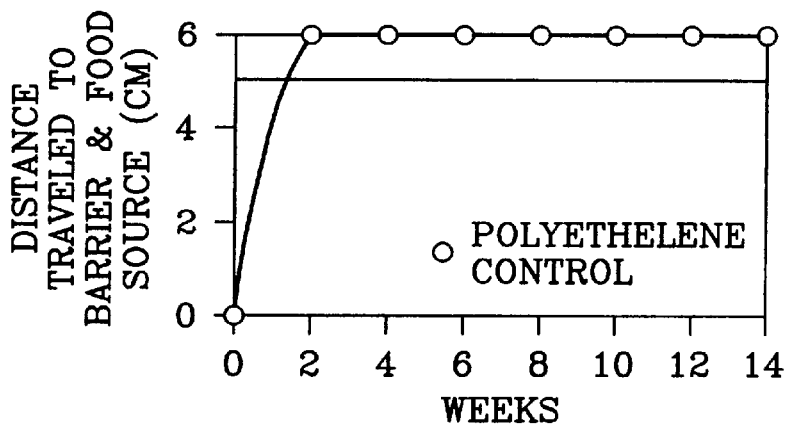
FIG. 20*a* is a graph of termite penetration versus time for a polyethylene control.
Figure 20B:
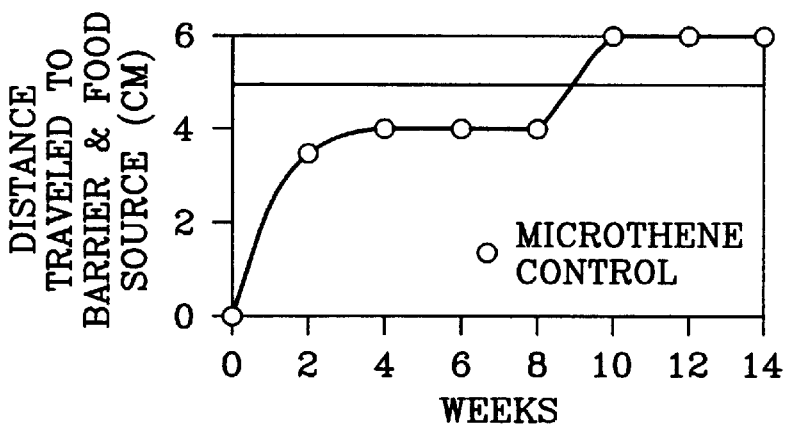
FIG. 20*b* is a graph of termite penetration versus time for a microthene control.
Figure 20C:
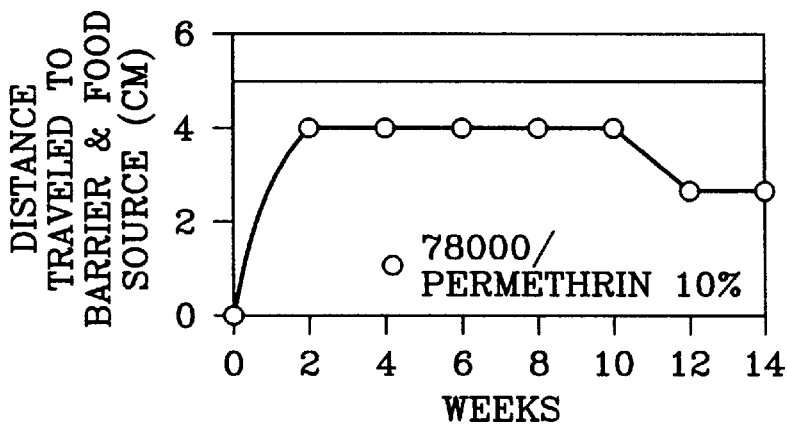
FIG. 20*c* is a graph of termite penetration versus time for HDPE with permethrin.
Figure 20D:
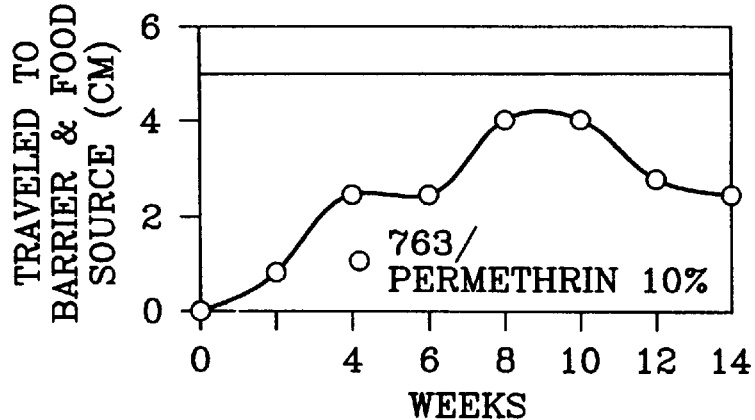
FIG. 20*d* is a graph of termite penetration versus time for LDPE with permethrin.
Figure 20E:
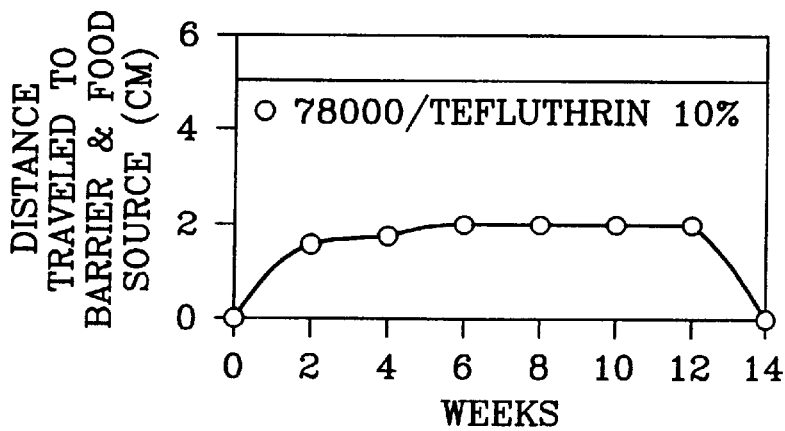
FIG. 20*e* is a graph of termite penetration versus time for HDPE with tefluthrin.
Figure 20F:
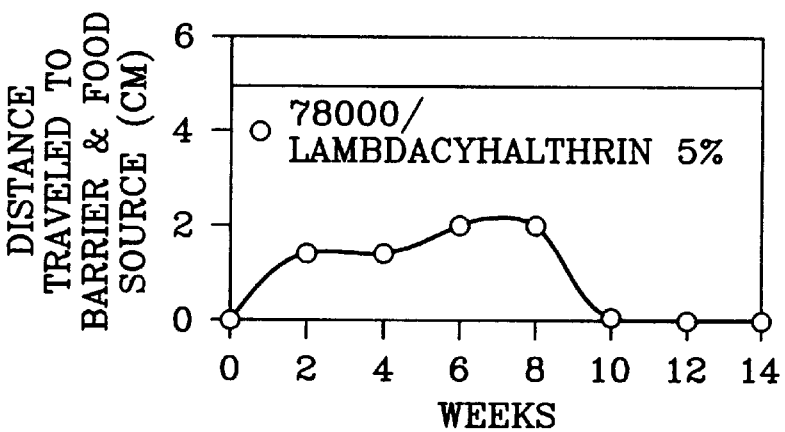
FIG. 20*f* is a graph of termite penetration versus time for HDPE with 5% lambdacyhalthrin.
Figure 20G:
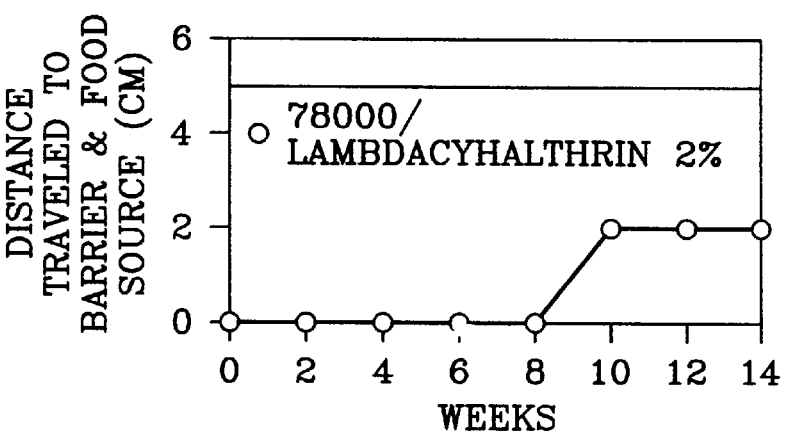
FIG. 20*g* is a graph of termite penetration versus time for HDPE with 2% lambdacyhalthrin.
Figure 20H:
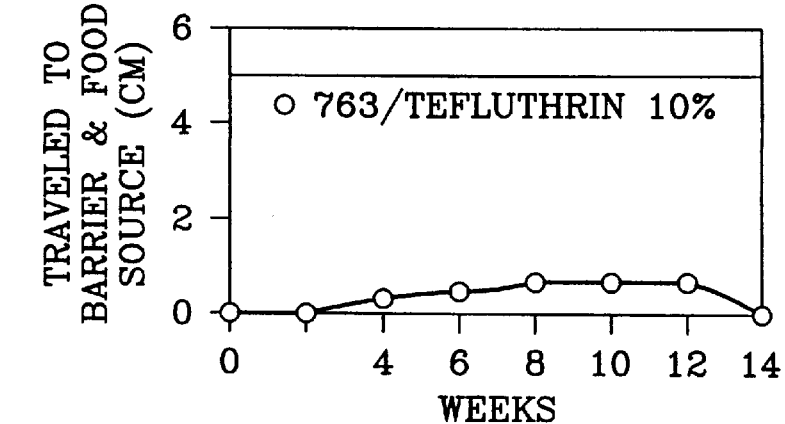
FIG. 20*h* is a graph of termite penetration versus time for LDPE with tefluthrin.
Figure 20I:
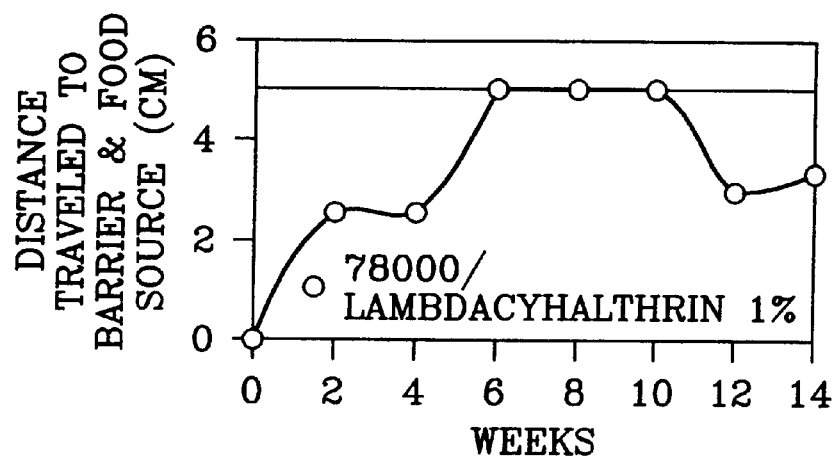
FIG. 20*i* is a graph of termite penetration versus time for HDPE with 1% lambdacyhalthrin.
Figure 20J:
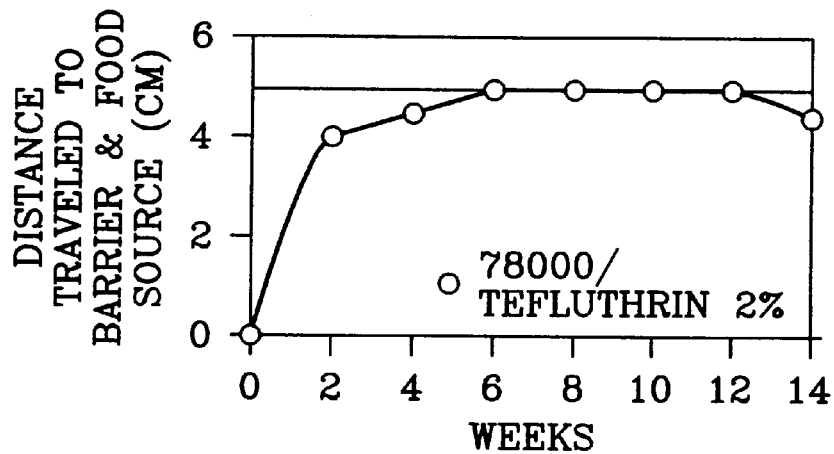
FIG. 20*j* is a graph of termite penetration versus time for HDPE with 2% tefluthrin.

Controlled release devices were also tested against termites. Active chemicals used were pyrethroids, permethrin, tefluthrin, and lamdacyhalthrin. The ratio of active chemical to carbon black was :2:1 by weight. The polymers used were LDPE (polyethylene 763) and HDPE (polyethylene 78000, Microthene). Test assemblies were made using a tube 10 cm in length. Termites were placed at one end (0.0 cm), a polymer barrier in the center (5.0 cm), and food opposite the termites (6.0 cm). Results are shown in FIGS. 20a–20j. Termite penetration of the control barriers having no active chemical occurred in 2 weeks for LDPE and 10 weeks for HDPE. No penetration occurred through any barrier having an active chemical over a 14 week period. Termite proximity to a barrier having an active chemical varied with the amount of active chemical released from the polymer. An effort was made to reduce release rate to permit the termites to approach the barrier but not penetrate the barrier. FIGS. 20i and 20j are for lamdacyhalthrin 1 wt % in HDPE and tefluthirin 2 wt % in HDPE respectively and demonstrate that no penetration occurred for reduced release rate systems.

For termites, it is preferred to deploy a sheet of controlled release product. Sheets range from about 10 mil to about 60 mil in thickness. Release rates resulting in longevities from about 2 years to over 60 years are achievable and predictable given the polymer, active chemical, carrier, concentrations thereof and operating temperature. For HDPE, tefluthrin, lambdacyhalthrin, permethrin and carbon black with a weight ratio of active chemical to carbon black of 1:1, sheet thickness of 60 mil, 0.05 wt % active chemical, longevity is about 13 years at 23° C. and about 45 years at 15° C. By increasing carbon black to 1:2, longevity is increased to about 60 years at 15° C. If the sheet is deployed beneath the ground surface, then longevity increases because the soil adjacent the sheet holds the released active chemical thereby decreasing the concentration gradient at the sheet surface that can result in longevity as high as from 77–85 years at 15° C.

Decreasing sheet thickness by half reduces longevity by about half.

Decreasing thickness from 60 mil to 10 mil reduces longevity by about a factor of 7.

Increasing active chemical concentration to 0.1 wt % increases longevity by about 50%.

100% Insect Lethality

The problem to be addressed by this aspect of the present invention is to achieve near 100% pest lethality while avoiding toxcicity to humans. This problem statement translates to a product having a surface concentration of an active chemical from about 2 ug/cm$^2$ to about 15 ug/cm$^2$. Further, it is desired that the controlled release product have a functional longevity from about 6 months to about 12 months.

According to a second aspect of the present invention, a microsponge of polymer holds active chemical permitting the active chemical to wet the surface of the microsponge without dripping from or crystallizing on the surface so that as an insect contacts the surface, active chemical is removed from the surface onto the insect. The active chemical from within the microsponge replenishes the location(s) on the surface where active chemical has been removed. The microsponge polymer has a formulation that would lead to a medium hardness (durometer) from about 60A to about 55D. However, the microsponge is not abrasion resistant so that even the clawed appendages of a cockroach are able to leave delible marks in the surface of the microsponge.

The microsponge is achieved by a method of making a controlled release device having a polymer and an active chemical having the steps of:

(a) selecting an amine curable elastomer pre-polymer;

(b) heating the pre-polymer making a first solution;

(c) heating and mixing a trialkanolamine with a soft segment cross-linker making a second solution;

(d) mixing the active chemical into either the first solution, second solution or both; and (e) pouring said second solution together with said first solution into a combined solution and continuing heating while mixing said combined solution into a castable mixture; and (e) casting said castable mixture.

In a preferred embodiment, the active chemical is mixed into the first solution. An alternative embodiment is to mix the active chemical with the soft segment cross-linker then mix with the trialkanolamine for the second solution and the first solution has only amine curable pre-polymer.

Amine curable elastomer pre-polymers include casting urethanes and other thermoset elastomers. Casting urethanes are thermoset plastics including but not limited to solithane, and combinations thereof. Thermoset elastomers include but are not limited to polyisoprene (a vulcanized crosslinked rubber), a blend of epoxy resin with carboxylated latex (Shell Hycar), and combinations thereof.

A carrier is not needed for castable pre-polymers, specifically casting urethanes, thermoset urethanes, and liquid crystal polyesters because these polymers have a combination of hard segments and soft segments that creates free volume structures within the polymers referred to herein as microsponge. These structures can act as reservoirs for the active ingredients without the need for carriers.

The active chemical is first mixed with the pre-polymer to obtain a substantially homogeneous first mixture or first solution of active chemical in the pre-polymer. It is preferred to avoid mixing active chemical into soft segment cross linker because when the soft segment cross linker and pre-polymer are mixed, there may be insufficient time to obtain a substantially homogeneous mix before substantial cross linking has occurred.

It was found that using low trialkanolamine, specifically triisopropanolamine (TIPA), typically done in making cast urethanes, resulted in excessively high release rates of active chemical from the cast urethane permitting formation of crystals of active chemical on the surface of the cast urethane. It was discovered that by combining a soft segment cross linker with a high amount of trialkanolamine that adequate release rates were obtained without formation of crystals.

If the active chemical has functional groups that react with the amine curable pre-polymer, (eg hydroxyl group(s), amine(s)), mixing the active chemical with the amine curable pre-polymer in the first solution will expose the active chemical to the amine curable pre-polymer and may react with it thereby destroying or diminishing active chemical molecules and possibly also reducing polymerization of the final product. Accordingly, for active chemicals with functional groups reactive with amine curable pre-polymer, it is preferred that the active chemical be first mixed with the amine (eg trialkanolamine) and soft segment cross linker (eg C113) in the first solution. Then, when the amine curable pre-polymer (eg isocyanate) is added, the amine curable pre-polymer it tends to react first with the soft segment cross linker thereby reducing the amount of unwanted reaction with the active chemical.

EXAMPLE 5

Several formulations were made and release rates measured. Results are shown in TABLE E5-1, and TABLE E5-2. The Krayton and Polyisoprene were made simply by adding the active chemical (cyfluthrin) to a standard thermoset formulation. The reduced release rate is beneficial to longer life controlled release product.

TABLE E5-1

Formulation and Initial Release Rate for Selected Elastomer Based Controlled Release Products

| Active Chemical | Elastomer | Type | Initial Release Rate ug/cm$^2$/d |
|---|---|---|---|
| Cyfluthrin | | | |
| 33 wt % | Kraton D1101 | Thermoplastic | 91 |
| 33 wt % | Polyisoprene | Crosslinked Rubber | 54 |
| 33 wt % | Hycar[a] | Blend | 7 |

[a]Hycar is Shell epoxy 828/Hycar

TABLE E5-2

Formulation and Release Rate

| Active Chemical | Thermoset | Release Rate ug/cm$^2$/d |
|---|---|---|
| Deltamethrin | | |
| 15 wt % | Aromatic 80 A | 4.4 |
| 15 wt % | Pellethane 2102 80 A | 4.6 |
| 15 wt % | Pellethane 2012 55D | 5.4 |

TABLE E5-2-continued

Formulation and Release Rate

| Active Chemical | Thermoset | Release Rate ug/cm$^2$/d |
|---|---|---|
| 15 wt % | Pellethane 2101 55D + 5 wt % carbon black | 2 |
| 15 wt % | Aliphatic PS-49-100 | 5.6 |

Note that a carrier (carbon black) may be used to reduce release rate compared to no carrier.

Controlled Release Composition

According to a further aspect of the present invention, a controlled release composition having a urethane containing an active chemical may be an improved composition having (a) the urethane is a casting urethane having ur linkages;
(b) a soft segment cross-linker; and
(c) a trialkanolamine cross-linker/catalyst in an amount from about 1.0 wt % to about 5 wt %.

The casting urethane is preferably in an amount of at least 54 wt %. The soft segment cross linker is preferably in an amount up to about 26 wt %. The active chemical is in an amount from about 0.5 wt % to about 33 wt %.

Ur linkages include urethane linkages, urea linkages, or both.

CLOSURE

From the foregoing description one skilled in the art can easily ascertain the essential characteristics of this invention and without department from the spirit and scope of the invention thereof can make changes and modifications of the invention in order to adapt it to the various usages and conditions. It is intended that the scope of the invention be defined by the following claims including all equivalents which are intended to define this invention.

We claim:

1. A method for creating a barrier to entry of crawling or soil borne insects to provide long term protection of an area of ground, a space, or a structure from intrusion by said insects, said method comprising the following steps:

(a) placing a controlled release barrier at the entry points to said area, space, or structure, said barrier having an outside surface and comprising a polymeric matrix and a pesticide within said matrix, said matrix having an outside surface;

(b) allowing the pesticide to release onto the outside surface of the matrix and accumulate on said outside surface of the matrix, the release rate of the pesticide being greater than 0.4 $\mu$g/cm$^2$/day and less than 10 $\mu$g/cm$^2$/day, said rate being sufficient to deter the insects so as to protect said area, space, or said structure from intrusion by said crawling or soil borne insects.

2. The method as recited in claim 1, wherein the polymeric matrix is selected from the group consisting of silicones, EVA, urethanes, polyurethanes, acrylonitrile, butadiene, acrylic rubber, isoprene and styrene-vinyl-rubber.

3. The method as recited in claim 1, wherein the polymeric matrix further includes a carrier for controlling the release rate.

4. The method as recited in claim 3, wherein the carrier is selected from the group consisting of carbon black, clay, amorphous silica and combinations thereof.

5. The method as recited in claim 4, wherein the carrier is carbon black.

6. The method as recited in claim 3, wherein the concentration of the carrier is from about 3 to about 5 percent per total weight of the matrix.

7. The method as recited in claim 3, wherein the concentration of the carrier is from about 2 to about 7 percent per total weight of the matrix.

8. The method as recited in claim 1, wherein the concentration of the pesticide is in the range from about 2 to about 15 percent of the total weight of the matrix.

9. The method as recited in claim 8, wherein the concentration of the pesticide is from about 5 to about 10 percent of the total weight of the matrix.

10. The method as recited in claim 1, wherein said pesticide is deltamethrin.

11. The method as recited in claim 1, wherein said pesticide is cypermethrin.

12. The method as recited in claim 1, wherein said pesticide is lambdacyhalothrin.

13. The method as recited in claim 1, wherein said pesticide is tefluthrin.

14. The method as recited in claim 1, wherein said pesticide is permethrin.

15. The method as recited in claim 1, wherein the matrix continues releasing the pesticide for a time period from about 6 months to 5 years.

16. The method as recited in claim 1, wherein the polymeric matrix is selected from the group consisting of silicones, EVA, urethanes, polyurethanes, acrylonitrile, butadiene, acrylic rubber, isoprene, high density polyethylene, low density polyethylene, vinyl acetate, polyester, santoprene, neoprene, polypropylene, polybutylene, epoxy polymers, polyamides, acrylate-styrene-acrylonitrile, aromatic polyesters, unsaturated polyesters, polyisoprene, styrene-vinyl-rubber, and copolymers thereof.

17. The method as recited in claim 1, wherein the polymeric matrix comprises low density polyethylene.

18. The method as recited in claim 1, wherein said pesticide is selected from the group consisting of tefluthrin, lambdacyhalothrin, cyfluthrin, deltamethrin, isofenphos, fenvalerate, cypermethrin, permethrin, pyrethrin, and combinations thereof.

19. The method as recited in claim 1, further comprising the step of forming the polymeric matrix into a strip, sheet, or a pellet.

20. The method as recited in claim 1, further comprising the step of forming the polymeric matrix into a polymeric sheet.

21. The method as recited in claim 1, wherein the barrier further comprises a second polymeric matrix.

22. The method as recited in claim 21, further comprising the step of forming the second polymeric matrix into a sheet.

23. The method as recited in claim 1, wherein the matrix continues releasing the pesticide for at least 6 years.

24. The method as recited in claim 1, wherein the polymeric matrix further comprises a fungicide.

25. The method as recited in claim 1, wherein the insects are termites.

26. The method of claim 1, wherein the barrier further comprises a layer laminated to the polymeric matrix.

27. The method of claim 26, wherein the additional layer is a metallized foil.

28. The method of claim 26, wherein the additional layer is an extruded polymer sheet.

29. The method of claim 1, wherein the barrier further comprises an insecticide-impervious sheet.

30. The method of claim 29, wherein the insecticide-impervious sheet is a metallized foil.

31. A method for creating a barrier to entry of crawling or soil borne insects to provide long term protection of an area of ground, a space, or a structure from intrusion by said insects, said method comprising the following steps:
  (a) incorporating a pesticide into a polymer;
  (b) forming the polymer into a polymeric matrix;
  (c) forming a controlled release barrier comprising the polymeric matrix, said matrix having an outside surface; and
  (d) allowing the pesticide to release onto the outside surface of the matrix and accumulate on the outside surface of the matrix, the release rate of the pesticide being greater than 0.4 $\mu g/cm^2/day$ and less than 10 $\mu g/cm^2/day$, said rate being sufficient to deter the insects so as to protect said area, space, or structure from intrusion by said crawling or soil borne insects.

32. The method as recited in claim 31, wherein the polymeric matrix is selected from the group consisting of silicones, EVA, urethanes, polyurethanes, acrylonitrile, butadiene, acrylic rubber, isoprene and styrene-vinyl-rubber.

33. The method as recited in claim 31, wherein the polymeric matrix further includes a carrier for controlling the release rate.

34. The method as recited in claim 33, wherein the carrier is selected from the group consisting of carbon black, clay, amorphous silica, and combinations thereof.

35. The method as recited in claim 33, wherein the carrier is carbon black.

36. The method as recited in claim 33, wherein the concentration of the carrier is from about 3 to about 5 percent per total weight of the matrix.

37. The method as recited in claim 33, wherein the concentration of the carrier is from about 2 to about 7 percent per total weight of the matrix.

38. The method as recited in claim 31, wherein the pesticide is selected from the group consisting of tefluthrin, lambdacyhalothrin, cyfluthrin, deltamethrin, isofenphos, fenvalerate, cypermethrin, permethrin, pyrethrin, and combinations thereof.

39. The method as recited in claim 31, wherein the pesticide is lambdacyhalothrin.

40. The method as recited in claim 31, wherein the concentration of the pesticide is from about 2 to about 15 percent per total weight of the matrix.

41. The method as recited in claim 31, wherein the concentration of the pesticide is from about 5 to about 10 percent per total weight of the matrix.

42. The method as recited in claim 31, wherein the polymeric matrix is selected from the group consisting of silicones, EVA, urethanes, polyurethanes, acrylonitrile, butadiene, acrylic rubber, isoprene, high density polyethylene, low density polyethylene, vinyl acetate, polyester, santoprene, neoprene, polypropylene, polybutylene, epoxy polymers, polyamides, acrylate-styrene-acrylonitrile, aromatic polyesters, unsaturated polyesters, polyisoprene, styrene-vinyl-rubber, and copolymers thereof.

43. The method as recited in claim 31, wherein the polymeric matrix comprises low density polyethylene.

44. The method as recited in claim 31, wherein the matrix continues releasing the pesticide for at least 6 years.

45. The method as recited in claim 31, wherein the matrix continues releasing the pesticide for a time period from about 6 months to 5 years.

46. The method as recited in claim 31, further comprising the step of forming the polymeric matrix into a strip, sheet, or a pellet.

47. The method as recited in claim 31, further comprising the step of forming the polymeric matrix into a polymeric sheet.

48. The method as recited in claim 31, wherein the barrier further comprises a second polymeric matrix.

49. The method as recited in claim 48, further comprising the step of forming the second polymeric matrix into a sheet.

50. The method as recited in claim 31, wherein the polymeric matrix further comprises a fungicide.

51. The method as recited in claim 31, wherein the insects are termites.

52. The method of claim 31, wherein the barrier further comprises a layer laminated to the polymeric matrix.

53. The method of claim 52, wherein the additional layer is a metallized foil.

54. The method of claim 52, wherein the additional layer is an extruded polymer sheet.

55. The method of claim 31, wherein the barrier further comprises an insecticide-impervious sheet.

56. The method of claim 55, wherein the insecticide-impervious sheet is a metallized foil.

57. The method of claim 47, further comprising the step of laminating an additional layer to the polymeric sheet.

* * * * *